US009517059B2

(12) United States Patent
Castro

(10) Patent No.: US 9,517,059 B2
(45) Date of Patent: Dec. 13, 2016

(54) ARTICULATING SURGICAL INSTRUMENTS AND METHOD OF DEPLOYING THE SAME

(71) Applicant: Michael Salvatore Castro, Plymouth, MA (US)

(72) Inventor: Michael Salvatore Castro, Plymouth, MA (US)

(73) Assignee: Medrobotics Corporation, Raynham, MA (US)

( * ) Notice: Subject to any disclaimer, the term of this patent is extended or adjusted under 35 U.S.C. 154(b) by 0 days.

(21) Appl. No.: 14/888,541

(22) PCT Filed: May 20, 2014

(86) PCT No.: PCT/US2014/038701
§ 371 (c)(1),
(2) Date: Nov. 2, 2015

(87) PCT Pub. No.: WO2014/189876
PCT Pub. Date: Nov. 27, 2014

(65) Prior Publication Data
US 2016/0074028 A1    Mar. 17, 2016

Related U.S. Application Data

(60) Provisional application No. 61/825,297, filed on May 20, 2013, provisional application No. 61/909,605, (Continued)

(51) Int. Cl.
*A61B 17/00* (2006.01)
*A61B 17/29* (2006.01)
*A61B 18/14* (2006.01)

(52) U.S. Cl.
CPC ......... *A61B 17/00234* (2013.01); *A61B 17/29* (2013.01); *A61B 17/2909* (2013.01);
(Continued)

(58) Field of Classification Search
CPC ............... A61B 2017/2946; A61B 2017/2929; A61B 2017/00314; A61B 2017/2923; A61B 2017/00323; A61B 2017/293; A61B 2017/003; A61B 2017/00327; A61B 2017/00407; A61B 2017/00424; A61B 2017/0046; A61B 2017/291; A61B 17/00234; A61B 17/29; A61B 17/2909; A61B 18/1445; A61B 18/1442; A61B 18/1492; A61B 2018/1455; A61B 2034/306; A61B 2034/301; A61B 2034/302; A61B 2017/2918; A61B 2017/2922; A61B 2017/2925; A61B 2090/508; A61B 34/30; A61B 34/71
See application file for complete search history.

(56) References Cited

U.S. PATENT DOCUMENTS 5,507,296 A    4/1996  Bales et al.
5,524,180 A    6/1996  Wang et al.
(Continued)

FOREIGN PATENT DOCUMENTS

| EP | 0653922 | 11/2005 |
|---|---|---|
| EP | 1015068 | 9/2011 |
| WO | 2011127137 | 10/2011 |

OTHER PUBLICATIONS

International Search Report and the Written Opinion dated Sep. 5, 2014, issued in corresponding International Patent Application No. PCT/US2014/038701.
(Continued)

*Primary Examiner* — Katherine M Shi
*Assistant Examiner* — Mohamed Gabr
(74) *Attorney, Agent, or Firm* — Onello & Mello, LLP

(57) ABSTRACT

A surgical instrument comprises a steering mechanism. The steering mechanism comprises a handle at a proximal end of
(Continued)

the surgical instrument. The handle includes a plurality of controls for controlling a movement of the surgical instrument. The steering mechanism also comprises a hub that rotatably mates with the handle and a housing positioned about the hub. The handle, the housing, and the hub communicate with each other to provide at least a first degree of freedom and a second degree of freedom. An articulation region is at a distal end of the surgical instrument. A movement of the steering mechanism handle in one and only one of the first or second degrees of freedom relative to at least one of the housing or the hub translates to a movement of the articulation region in a single plane of motion.

33 Claims, 10 Drawing Sheets

Related U.S. Application Data filed on Nov. 27, 2013, provisional application No. 61/921,858, filed on Dec. 30, 2013.

(52) U.S. Cl.
CPC ....... *A61B 18/1442* (2013.01); *A61B 18/1445* (2013.01); *A61B 2017/00314* (2013.01); *A61B 2017/00327* (2013.01); *A61B 2017/291* (2013.01); *A61B 2017/2923* (2013.01); *A61B 2017/2929* (2013.01); *A61B 2017/2946* (2013.01)

(56) References Cited

U.S. PATENT DOCUMENTS

| | | | |
|---|---|---|---|
| 5,759,151 A | 6/1998 | Sturges | |
| 5,815,640 A | 9/1998 | Wang et al. | |
| 5,841,950 A | 11/1998 | Wang et al. | |
| 5,907,664 A | 5/1999 | Wang et al. | |
| 5,916,147 A | 6/1999 | Boury | |
| 6,080,181 A | 6/2000 | Jensen et al. | |
| 6,132,368 A | 10/2000 | Cooper | |
| 6,346,072 B1 | 2/2002 | Cooper | |
| 6,837,846 B2 | 1/2005 | Jaffe et al. | |
| 6,837,847 B2 | 1/2005 | Ewers et al. | |
| 7,357,774 B2 | 4/2008 | Cooper | |
| 7,789,875 B2 | 9/2010 | Brock et al. | |
| 7,819,885 B2 | 10/2010 | Cooper | |
| 7,850,642 B2 | 12/2010 | Moll et al. | |
| 7,854,109 B2 | 12/2010 | Zubiate et al. | |
| 7,854,738 B2 | 12/2010 | Lee et al. | |
| 7,867,241 B2 | 1/2011 | Brock et al. | |
| 7,946,546 B2 | 5/2011 | Zubiate et al. | |
| 8,100,031 B2 | 1/2012 | Zubiate et al. | |
| 8,192,422 B2 | 6/2012 | Zubiate et al. | |
| 8,459,138 B2 | 6/2013 | Zubiate et al. | |
| 2002/0091374 A1 | 7/2002 | Cooper | |
| 2005/0021050 A1 | 1/2005 | Cooper | |
| 2006/0111616 A1 | 5/2006 | Danitz | |
| 2007/0093790 A1* | 4/2007 | Downey | A61B 17/00234 606/1 |
| 2007/0221700 A1 | 9/2007 | Ortiz et al. | |
| 2008/0065116 A1* | 3/2008 | Lee | A61B 17/2909 606/142 |
| 2008/0147091 A1 | 6/2008 | Cooper | |
| 2008/0245173 A1 | 10/2008 | Schwerin et al. | |
| 2008/0255420 A1* | 10/2008 | Lee | A61B 17/2909 600/137 |
| 2008/0287963 A1 | 11/2008 | Rogers et al. | |
| 2009/0143639 A1 | 6/2009 | Stark | |
| 2009/0171151 A1 | 7/2009 | Choset et al. | |
| 2009/0259141 A1 | 10/2009 | Ewers et al. | |
| 2010/0016852 A1* | 1/2010 | Manzo | A61B 34/71 606/46 |
| 2010/0175940 A1 | 7/2010 | Taneda et al. | |
| 2010/0179540 A1* | 7/2010 | Marczyk | A61B 18/1445 606/41 |
| 2011/0021871 A1 | 1/2011 | Berkelaar | |
| 2011/0028990 A1 | 2/2011 | Cooper | |
| 2011/0066161 A1 | 3/2011 | Cooper | |
| 2011/0152613 A1 | 6/2011 | Zubiate et al. | |
| 2011/0184241 A1 | 7/2011 | Zubiate et al. | |
| 2011/0198386 A1 | 8/2011 | Viola | |
| 2011/0238108 A1* | 9/2011 | Peine | A61B 17/00234 606/205 |
| 2011/0313243 A1 | 12/2011 | Zubiate et al. | |
| 2012/0078248 A1 | 3/2012 | Worrell et al. | |
| 2012/0109186 A1 | 5/2012 | Parrott et al. | |
| 2012/0138834 A1 | 6/2012 | Tortel et al. | |
| 2012/0253326 A1* | 10/2012 | Kleyman | A61B 34/30 606/1 |
| 2012/0265220 A1 | 10/2012 | Menn | |
| 2013/0023915 A1* | 1/2013 | Mueller | A61B 17/29 606/170 |
| 2014/0336675 A1 | 11/2014 | Menn | |
| 2016/0074028 A1* | 3/2016 | Castro | A61B 17/2909 606/130 |

OTHER PUBLICATIONS

International Search Report and the Written Opinion dated Oct. 12, 2012, issued in corresponding International Patent Application No. PCT/US2012/032279.

International Search Report dated Nov. 8, 2013 issued in corresponding International Application No. PCT/US2013/043858.

Extended European Search Report dated Aug. 20, 2014, issued in corresponding International Patent Application No. PCT/US2012/032279.

Office Action dated Jul. 30, 2015 from related family application EP 12768046.0.

\* cited by examiner

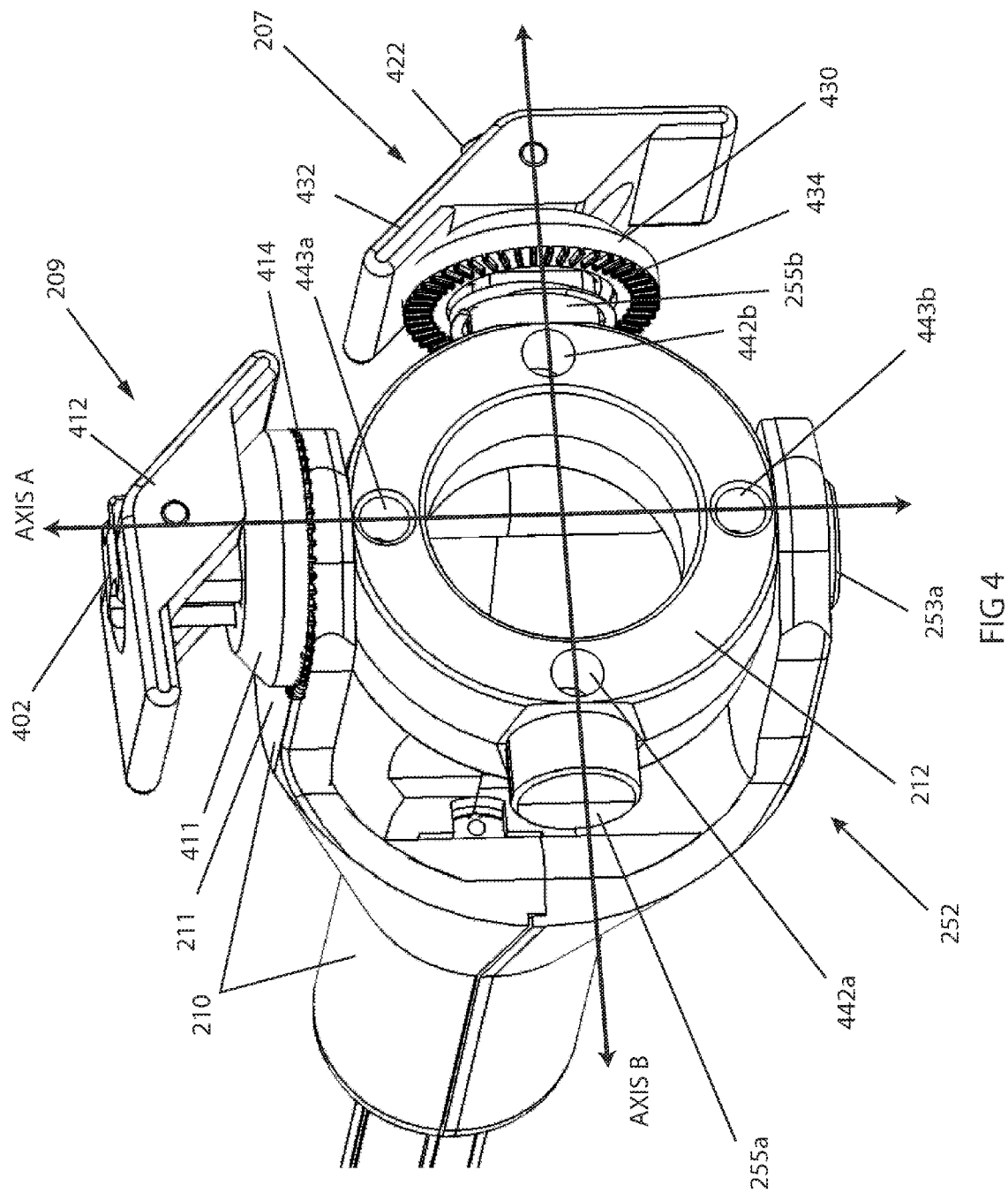

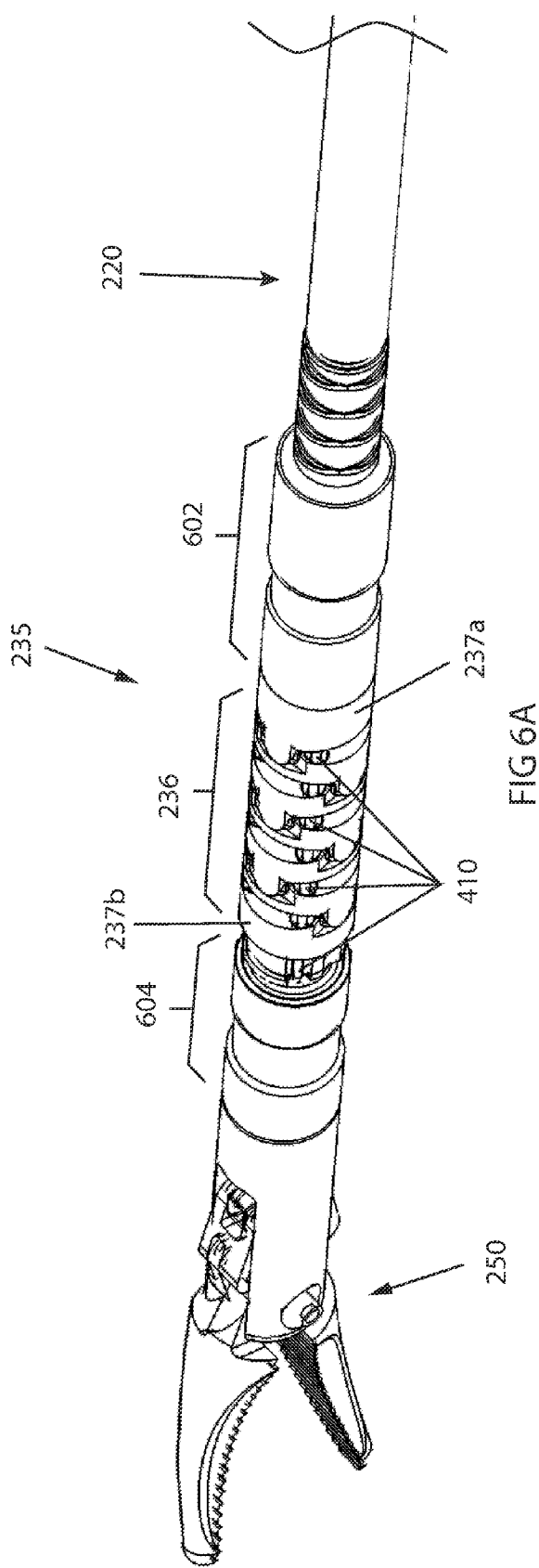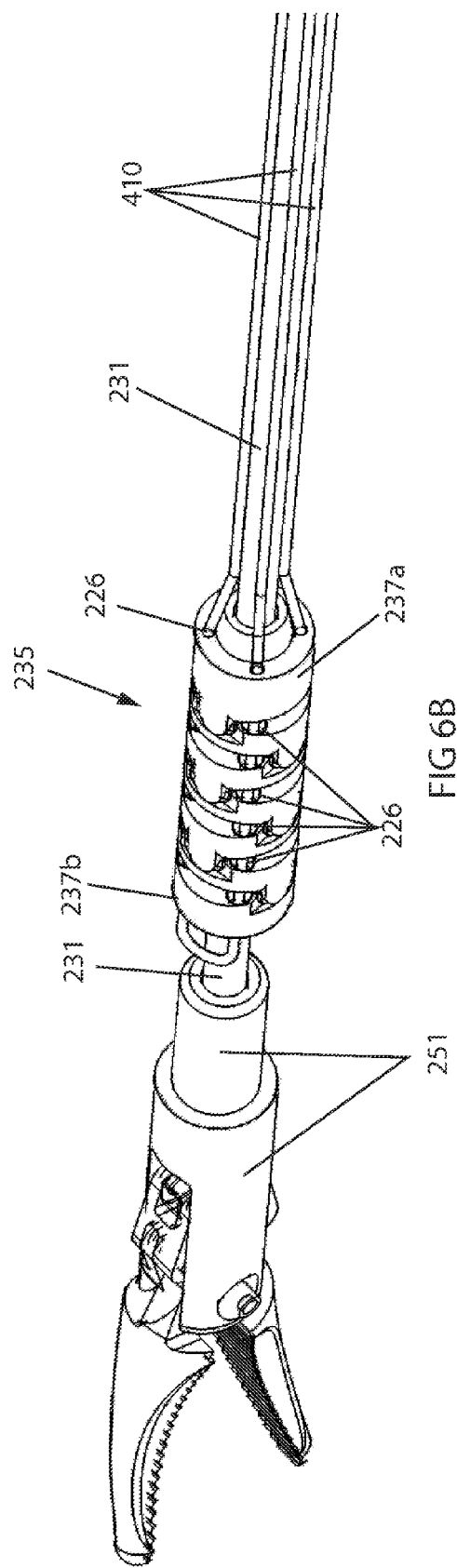

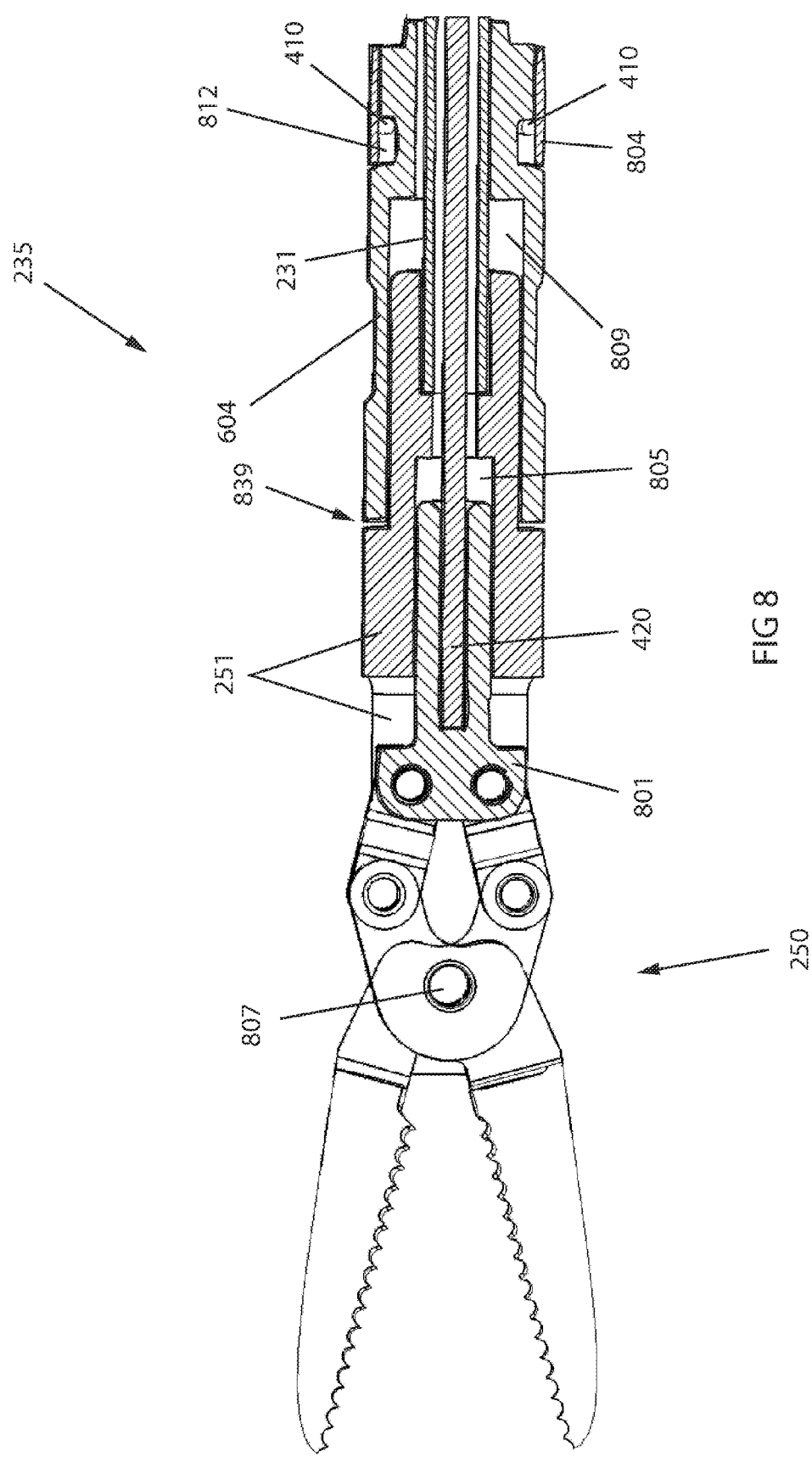

ARTICULATING SURGICAL INSTRUMENTS AND METHOD OF DEPLOYING THE SAME

RELATED APPLICATIONS

This application claims the benefit of U.S. Provisional Application No. 61/921,858, filed Dec. 30, 2013, the content of which is incorporated herein by reference in its entirety.

This application claims the benefit of U.S. Provisional Application No. 61/825,297, filed May 20, 2013, the content of which is incorporated herein by reference in its entirety.

This application claims the benefit of U.S. Provisional Application No. 61/909,605, filed Nov. 27, 2013, the content of which is incorporated herein by reference in its entirety.

This application is related to U.S. Provisional Application No. 61/406,032, filed Oct. 22, 2010, the content of which is incorporated herein by reference in its entirety.

This application is related to PCT Application No PCT/US2011/057282, filed Oct. 21, 2011, the content of which is incorporated herein by reference in its entirety.

This application is related to U.S. patent application Ser. No. 13/880,525, filed Apr. 19, 2013, the content of which is incorporated herein by reference in its entirety. This application is related to U.S. Provisional Application No. 61/492,578, filed Jun. 2, 2011, the content of which is incorporated herein by reference in its entirety.

This application is related to PCT Application No. PCT/US12/40414, filed Jun. 1, 2012, the content of which is incorporated herein by reference in its entirety.

This application is related to U.S. patent application Ser. No. 14/119,316, filed Nov. 21, 2013, the content of which is incorporated herein by reference in its entirety.

This application is related to U.S. Provisional Application No. 61/412,733, filed Nov. 11, 2010, the content of which is incorporated herein by reference in its entirety.

This application is related to PCT Application No PCT/US2011/060214, filed Nov. 10, 2011, the content of which is incorporated herein by reference in its entirety.

This application is related to U.S. patent application Ser. No. 13/884,407, filed May 9, 2013, the content of which is incorporated herein by reference in its entirety.

This application is related to U.S. Provisional Application No. 61/472,344, filed Apr. 6, 2011, the content of which is incorporated herein by reference in its entirety.

This application is related to PCT Application No. PCT/US12/32279, filed Apr. 5, 2012, the content of which is incorporated herein by reference in its entirety.

This application is related to U.S. patent application Ser. No. 14/008,775, filed Sep. 30, 2013, the content of which is incorporated herein by reference in its entirety.

This application is related to U.S. Provisional Application No. 61/534,032 filed Sep. 13, 2011, the content of which is incorporated herein by reference in its entirety.

This application is related to PCT Application No. PCT/US12/54802, filed Sep. 12, 2012, the content of which is incorporated herein by reference in its entirety.

This application is related to U.S. patent application Ser. No. 14/343,915, filed Mar. 10, 2014, the content of which is incorporated herein by reference in its entirety.

This application is related to U.S. Provisional Application No. 61/368,257, filed Jul. 28, 2010, the content of which is incorporated herein by reference in its entirety.

This application is related to PCT Application No PCT/US2011/044811, filed Jul. 21, 2011, the content of which is incorporated herein by reference in its entirety.

This application is related to U.S. patent application Ser. No. 13/812,324, filed Jan. 25, 2013, the content of which is incorporated herein by reference in its entirety.

This application is related to U.S. Provisional Application No. 61/578,582, filed Dec. 21, 2011, the content of which is incorporated herein by reference in its entirety.

This application is related to PCT Application No. PCT/US12/70924, filed Dec. 20, 2012, the content of which is incorporated herein by reference in its entirety.

This application is related to U.S. Provisional Application No. 61/681,340, filed Aug. 9, 2012, the content of which is incorporated herein by reference in its entirety.

This application is related to PCT Application No. PCT/US13/54326, filed Aug. 9, 2013, the content of which is incorporated herein by reference in its entirety.

This application is related to U.S. Provisional Application No. 61/751,498, filed Jan. 11, 2013, the content of which is incorporated herein by reference in its entirety.

This application is related to PCT Application No. PCT/US14/01808, filed Jan. 9, 2014, the content of which is incorporated herein by reference in its entirety.

This application is related to U.S. Provisional Application No. 61/656,600, filed Jun. 7, 2012, the content of which is incorporated herein by reference in its entirety.

This application is related to PCT Application No. PCT/US13/43858, filed Jun. 3, 2013, the content of which is incorporated herein by reference in its entirety.

This application is related to U.S. Provisional Application No. 61/818,878, filed May 2, 2013, the content of which is incorporated herein by reference in its entirety.

This application is related to PCT Application No. PCT/US14/36571, filed May 2, 2014, the content of which is incorporated herein by reference in its entirety.

This application is related to U.S. patent application Ser. No. 11/630,279, filed Dec. 20, 2006, published as U.S. Patent Application Publication No. 2009/0171151, the content of which is incorporated herein by reference in its entirety.

TECHNICAL FIELD

The present inventive concepts generally relate to the field of surgical tools, and more particularly, to articulating surgical tools, methods of deploying articulating surgical tools and tool sheaths, and methods of forming the same.

BACKGROUND

As less invasive medical techniques and procedures become more widespread, medical professionals, such as surgeons, may require articulating surgical tools, such as endoscopes, to perform such less invasive medical techniques and procedures from outside the human body. However, conventional articulating surgical tools, such as endoscopes and other types of tools, are limited with respect to movement about various planes.

SUMMARY

In one aspect, provided is a surgical instrument comprising a steering mechanism. The steering mechanism comprises a handle at a proximal end of the surgical instrument. The handle includes a plurality of controls for controlling a movement of the surgical instrument. The steering mechanism also comprises a hub that rotatably mates with the handle; and a housing positioned about the hub. The handle, the housing, and the hub communicate with each other to provide at least a first degree of freedom and a second degree of freedom. An articulation region is at a distal end of the surgical instrument. A movement of the steering mechanism handle in one and only one of the first or second degrees of freedom relative to at least one of the housing or the hub translates to a movement of the articulation region in a single plane of motion.

In some embodiments, the steering mechanism further comprises a locking mechanism controlled by at least one locking control of the plurality of controls of the handle, the locking mechanism constructed and arranged to disable one of the first and second degrees of freedom to limit a movement of the articulation region in the single plane of motion.

In some embodiments, the locking mechanism comprises two locking mechanisms controlled by the at least one locking control, and wherein the two locking mechanisms, when activated, are constructed and arranged to disable one or both of the first and second degrees of freedom to prevent steering of the articulation region.

In some embodiments, the locking mechanism includes a first lock that prevents the steering mechanism from articulating with the first degree of freedom and a second lock that prevents the steering mechanism from articulating with the second degree of freedom.

In some embodiments, the hub includes a first post and a second post along a first articulating axis, and wherein the first lock includes a locking ring and a cam clamp that applies a force to the locking ring, which prevents the housing from rotating about the first articulating axis.

In some embodiments, the surgical instrument further comprises a set of interdigitating teeth between the locking ring and the housing. The locking ring applies a force at the interdigitating teeth to prevent a rotation of the housing about the first articulating axis.

In some embodiments, the first articulating axis is a vertical axis, and wherein a rotation of the hub about the vertical axis provides a horizontal control of the steerable portion.

In some embodiments, the hub includes a third post and a fourth post along a second articulating axis orthogonal to the first articulating axis, and wherein the second lock includes a locking ring and a cam clamp that applies a force to the locking ring, which prevents the housing from rotating about the second articulating axis.

In some embodiments, the surgical instrument further comprises a set of interdigitating teeth between the locking ring and the housing. The locking ring applies a force at the interdigitating teeth to prevent a rotation of the handle about the second articulating axis.

In some embodiments, the second articulating axis is a horizontal axis, and wherein a rotation of the handle about the horizontal axis of the hub provides a vertical control of the articulation region.

In some embodiments, an activation of either the first lock or the second lock limits movement of the articulation region to the single plane of motion.

In some embodiments, an activation of both the first lock and the second lock prevents steering of the instrument, and maintains a tool at a distal end of the instrument tool in a current position.

In some embodiments, the first lock and the second lock are disengaged, and the articulation region articulates in multiple planes of motion.

In some embodiments, the instrument comprises an end effector coupled to the articulation region, and wherein an articulation of the handle in accordance with two degrees of freedom permits the articulation region to be manipulated to reach anywhere on a surface of at least a partial sphere.

In some embodiments, the plurality of controls at the handle includes a ratcheting trigger for incrementally ratcheting the end effector at the distal end of the instrument.

In some embodiments, the plurality of controls at the handle includes a control in communication with a power source.

In some embodiments, the power source includes an RF power source.

In some embodiments, the plurality of controls at the handle includes a control in communication with a fluid source.

In some embodiments, the handle comprising one selected from the group consisting of: a palm-held grip, a thumb/index/middle finger grip, a pistol grip, a reciprocating trigger, and a scissor type.

In some embodiments, the surgical instrument further comprises a U-joint. The U-joint provides the first and second degrees of freedom between a combination of the handle, the hub, and the housing.

In some embodiments, the U-joint comprises a first hinge along a first axis, the first hinge providing the first degree of freedom between the handle and the housing about the first axis.

In some embodiments, the U-joint comprises a second hinge along a second axis orthogonal to the first axis, the second hinge providing the second degree of freedom between the hub and the handle about the second axis.

In some embodiments, surgical instrument further comprises a plurality of steering cables coupled between the housing and the articulation region. An articulation of the handle relative to the housing advances and retracts the plurality of steering cables, which move the articulation region in the single plane of motion or in multiple planes of motion.

In some embodiments, the plurality of steering cables comprise first and second steering cables that extend from the handle to the articulation region, the first and second steering cables constructed and arranged to move the articulation region relative to a first axis about the single plane of motion when the handle articulates at the first degree of freedom relative to the housing.

In some embodiments, the articulation region moves in the single plane of motion in response to a movement of at least one of the first or second steering cables in an axial direction between the handle and the articulation region.

In some embodiments, the movement of the at least one of the first or second steering cables in the axial direction is in response to a movement by the handle relative to the housing at the first degree of freedom.

In some embodiments, the hub includes first and second cable fastening locations that couple proximal ends of the first and second steering cables to the hub.

In some embodiments, the surgical instrument further comprises third and fourth steering cables that extend from the handle to the articulation region. The third and fourth steering cables are constructed and arranged to move the articulation region about a second axis orthogonal to the first axis.

In some embodiments, the articulation region moves in the single plane of motion in response to a movement of at least one of the third or fourth steering cables in an axial direction between the handle and the articulation region.

In some embodiments, the movement of the at least one of the third or fourth steering cables in the axial direction is in response to a movement by the handle relative to the hub in the second degree of freedom orthogonal to the first degree of freedom.

In some embodiments, the hub includes first and second cable pass-through holes and the handle includes first and second fastening locations, wherein the third and fourth steering cables extend through the first and second pass-through holes, respectively, and wherein proximal ends of the third and fourth steering cables are coupled to the handle.

In some embodiments, the handle includes a cable tensioning mechanism that adjusts a tension of the third and fourth steering cables at the proximal ends.

In some embodiments, the cable tensioning mechanism comprises a set screw movably positioned in a threaded socket in the housing, the set screw including an opening for receiving an end of at least one of the third or fourth steering cables, which is secured to the set screw.

In some embodiments, the cable tensioning mechanism further comprises a tightening tool that adjusts the position of the set screw relative to the socket to achieve a desired tension of the at least one of the third or fourth steering cables.

In some embodiments, the surgical instrument further comprises a support element having a proximal end coupled to the handle. A portion of the support element extends through the articulation region. The support element is constructed and arranged to rotate independently of the movement of the articulation region in the single plane of motion.

In some embodiments, the support element is constructed and arranged as a coil.

In some embodiments, the support element is constructed and arranged as a hollow tube.

In some embodiments, the surgical instrument further comprises a clevis between an end effector coupled to the articulation region and a distal end of the support element.

In some embodiments, the surgical instrument further comprises a longitudinal clearance between the clevis and a distal link segment of the articulation region. The longitudinal clearance is dimensioned in an axial direction of the surgical instrument to prevent contact between the clevis and the distal end of the first assembly when the force is imparted by the movement of an activation element coupled between the handle and an end effector at a distal end of the instrument.

In some embodiments, the steering mechanism further comprises a ratchet mechanism, a gearing mechanism, a trigger assembly, and a translating assembly, wherein the ratchet mechanism is configured to maintain the translating assembly in a series of linear positions.

In some embodiments, the handle comprises a rotation knob, and wherein the translation assembly is coupled to the rotation knob, the rotation knob attached to the support element, and providing a rotational force to the support element.

In some embodiments, the support element is constructed and arranged to rotate a functional element at a distal end of the support element.

In some embodiments, the rotation knob comprises a hole, and wherein the surgical instrument further comprises an activation element that is coupled to the translating assembly, and extends through the rotation knob hole and the support element to the functional element to activate a tool of the functional element.

In some embodiments, the activation element activates the tool by a handle control advancing or retracting the activation wire.

In some embodiments, movement of the activation element is induced by the handle.

In some embodiments, the activation element is constructed and arranged as a wire.

In some embodiments, the activation element is constructed and arranged as a cable.

In some embodiments, the activation element is constructed and arranged as a fiber.

In some embodiments, the activation element is formed of Teflon or graphite.

In some embodiments, the trigger assembly is coupled to the gearing mechanism, and wherein the translating assembly slides within the handle, and is translated via the gearing mechanism.

In some embodiments, the trigger assembly comprises a trigger and a spring which is biased to maintain the trigger in a position.

In some embodiments, wherein the trigger comprises an un-pulled position, such as in a position in which a tool coupled to the articulation region is in an open or un-activated position.

In some embodiments, the ratchet mechanism is constructed and arranged to resist the force of the trigger spring.

In some embodiments, the ratchet mechanism is constructed and arranged to be temporarily disengaged to release the translating assembly, or to be locked in a disengaged position such that the trigger controls the translating assembly.

In some embodiments, the controls include a ratchet selector control that activates and de-activates the ratchet mechanism.

In some embodiments, the translating assembly comprises a linear gear that mates with the gearing mechanism to drive the translating assembly proximally and distally within the handle.

In some embodiments, the ratchet mechanism comprises a ratchet lock, a release ramp, and a ratchet selector configured to position the ratchet lock.

In some embodiments, the translating assembly comprises a plurality of teeth, wherein in a first, engaged position, the ratchet lock engages the teeth, and wherein in a second, disengaged position, the release ramp slides beneath the ratchet lock disengaging the ratchet teeth, allowing the translating assembly to move freely.

In some embodiments, the ratchet selector includes a first securing projection and a second securing projection, wherein the handle includes a housing having a first notch and a second notch that frictionally engages with the first and second securing projection, respectively.

In some embodiments, the surgical instrument further comprises a rigid shaft coupled to the housing and a flexible shaft coupled between the rigid shaft and the articulation region. The rigid shaft surrounds the proximal end of the flexible shaft, the rigid shaft and the flexible shaft extending along a same axial direction as the articulation region.

In some embodiments, the rigid shaft is configured to be slidingly received by a separate support structure to support the instrument and to provide a resistive force during articulation of the handle to enable steering.

In some embodiments, the flexible shaft follows a path through a working channel of a robotic probe or through a supporting tool guide alongside a robotic probe.

In some embodiments, the articulation region comprises at least three segment links, wherein each segment link has a single degree of freedom with respect to an adjacent segment link, and wherein each of the at least three segment links is positioned along a central axis.

In some embodiments, the at least three segment links include a first end link, a second end link, and at least one central link between the first and second end links, the at least three segment links constructed and arranged to articulate relative to each other based on forces applied to a plurality of steering cables controlled by the handle.

In some embodiments, the plurality of steering cables extend from the handle to a distal end of the articulation region.

In some embodiments, each of the least three segment links includes a central hole positioned along the central axis and a plurality of holes positioned about a periphery of the segment link and extending along an axis parallel to the central axis, each hole receiving a steering cable of the plurality of steering cables.

In some embodiments, each steering cable has a distal end that extends through a hole in the second end link at an outermost region of the articulation region.

In some embodiments, the distal end of the steering cable terminates at a recess of a distal segment of the at least three segments.

In some embodiments, a first hole of the plurality of holes is positioned 90 degrees from a second hole relative to the central axis.

In some embodiments, a first hole of the plurality of holes is positioned 180 degrees from a second hole relative to the central axis.

In some embodiments, the plurality of steering cables include a horizontal steering cable extending through a first hole in at least one segment link, and a vertical steering cable extending through a second hole in the at least one segment link that is positioned 90 degrees from the first hole.

In some embodiments, the horizontal steering cable is constructed and arranged to move the articulation region in along a horizontal plane or a plane tangential to the horizontal plane, and wherein the vertical steering cable is constructed and arranged to move the articulation region in along a vertical plane or a plane tangential to the vertical plane.

In some embodiments, three segment links of the at least three segment links are constructed and arranged to have two degrees of freedom with respect to a movement.

In some embodiments, two segment links of the at least three segment links are constructed and arranged to have a single degree of freedom with respect to a movement.

In some embodiments, wherein each of the at least three segment links comprises a protrusion constructed and arranged to mate with a slot at an adjacent segment link of the at least three segment links.

In some embodiments, the protrusion of the each of the at least three segment links is orthogonal to a protrusion of the adjacent segment link.

In some embodiments, a protrusion of a first segment link of the at least three segment links extends along a first axis and a protrusion of an adjacent second segment link of the at least three segment links extends along a second axis orthogonal axis, wherein a slot in the adjacent second segment link extends along the first axis, wherein the first protrusion is mated with the slot, and wherein the second segment link at least partially rotates about the first axis in a single degree of freedom.

In some embodiments, each of the at least three segment links comprises a first protrusion and a second protrusion at 180 degrees relative to the first protrusion, each of the first and second protrusions constructed and arranged to mate with a slot at an adjacent segment link.

In some embodiments, the first and second protrusions are each orthogonal to a protrusion of the adjacent segment link.

In some embodiments, a first segment link having a protrusion is positioned at a slot of an adjacent second segment link, the slot having a length along which the protrusion moves, the protrusion centered at a first axis extending through the protrusion, and wherein at least one of the first segment link or the second segment link rotates about the first axis subject to the length of the slot.

In some embodiments, the slot of the second segment link is in a first surface, the second segment link includes a protrusion that extends from a second surface opposite the first surface, and the protrusion and the slot of the second segment are orthogonal to each other.

In some embodiments, the surgical instrument further comprises a third segment link having a slot that mates with the protrusion of the second segment link, the third segment link slot having a length along which the second segment link protrusion moves, the second segment link protrusion centered at a second axis orthogonal to the first axis and extending through the second segment link protrusion, and wherein at least one of the second segment link or the third segment link rotates about the second axis subject to the length of the slot.

In some embodiments, the surgical instrument further comprises an end effector coupled to the articulation region at the distal end of the surgical instrument.

In some embodiments, the end effector includes a housing and at least one tool.

In some embodiments, the at least one tool comprises at least one of: a grasper; a scissor; a cutter; a claw; or a knife.

In some embodiments, the at least one tool comprises at least one of: an ablator, a drug delivery apparatus, a radiation source, an EKG electrode, a pressure sensor, a blood sensor, a camera, a magnet, a heating element, an energy delivery element, and a cryogenic element.

In some embodiments, the surgical instrument further comprises a support element that extends along at least a portion of the instrument, through a central working channel of the articulation region, and terminates at the end effector housing.

In some embodiments, a rotation of the support element causes the end effector to rotate the orientation of the at least one tool.

In some embodiments, the rotation of the support element is independent of an orientation of the articulation region.

In some embodiments, the support element comprises a torque cable configured to avoid twisting during rotation.

In some embodiments, the surgical instrument further comprises an activation element coupled extending between the handle and the end effector, and further comprising a slide positioned between the end effector and a distal segment of the articulation region.

In some embodiments, the end effector housing is positioned about at least a portion of the slide.

In some embodiments, a force applied to the activation element retracts the slide into a recess in the end effector housing.

In some embodiments, the at least one tool is in a closed position in response to the retraction of the slide into the recess.

In some embodiments, a rotation of the support element translates to a rotation of the end effector housing relative to the recess.

In some embodiments, a force applied to the activation element moves the activation element in a distal direction towards the at least one tool.

In some embodiments, the at least one tool is in an open position in response to the movement of the activation element in the distal direction.

In another aspect, provided is a method for performing a medical procedure using the surgical instrument referred to herein.

In another aspect, provided is a system for performing a medical procedure comprising: an articulating probe including inner and outer sleeves and a surgical instrument. The surgical instrument comprises a steering mechanism. The steering mechanism comprises a handle at a proximal end of the surgical instrument. The handle includes a plurality of controls for controlling a movement of the surgical instrument. The steering mechanism also comprises a hub that rotatably mates with the handle; and a housing positioned about the hub. The handle, the housing, and the hub communicate with each other to provide at least a first degree of freedom and a second degree of freedom. An articulation region is at a distal end of the surgical instrument. A movement of the steering mechanism handle in one and only one of the first or second degrees of freedom relative to at least one of the housing or the hub translates to a movement of the articulation region in a single plane of motion.

BRIEF DESCRIPTION OF THE DRAWINGS

The foregoing and other objects, features and advantages of embodiments of the present inventive concepts will be apparent from the more particular description of preferred embodiments, as illustrated in the accompanying drawings in which like reference characters refer to the same elements throughout the different views. The drawings are not necessarily to scale, emphasis instead being placed upon illustrating the principles of the preferred embodiments.

FIG. 4 is a cutaway close-up view of the locking mechanism and the U-joint of the surgical instrument of FIGS. 1-3, in accordance with embodiments of the present inventive concepts;

FIGS. 6A and 6B are perspective views of a distal end of the surgical instrument of FIGS. 1-5;

FIG. 8 is a cutaway side view of a distal end of a surgical instrument, in accordance with an embodiment.

DETAILED DESCRIPTION OF EMBODIMENTS

The terminology used herein is for the purpose of describing particular embodiments and is not intended to be limiting of the inventive concepts. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

It will be understood that, although the teens first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on" or "connected" or "coupled" to another element, it can be directly on or above, or connected or coupled to, the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.). When an element is referred to herein as being "over" another element, it can be over or under the other element, and either directly coupled to the other element, or intervening elements may be present, or the elements may be spaced apart by a void or gap.

Figure 1:
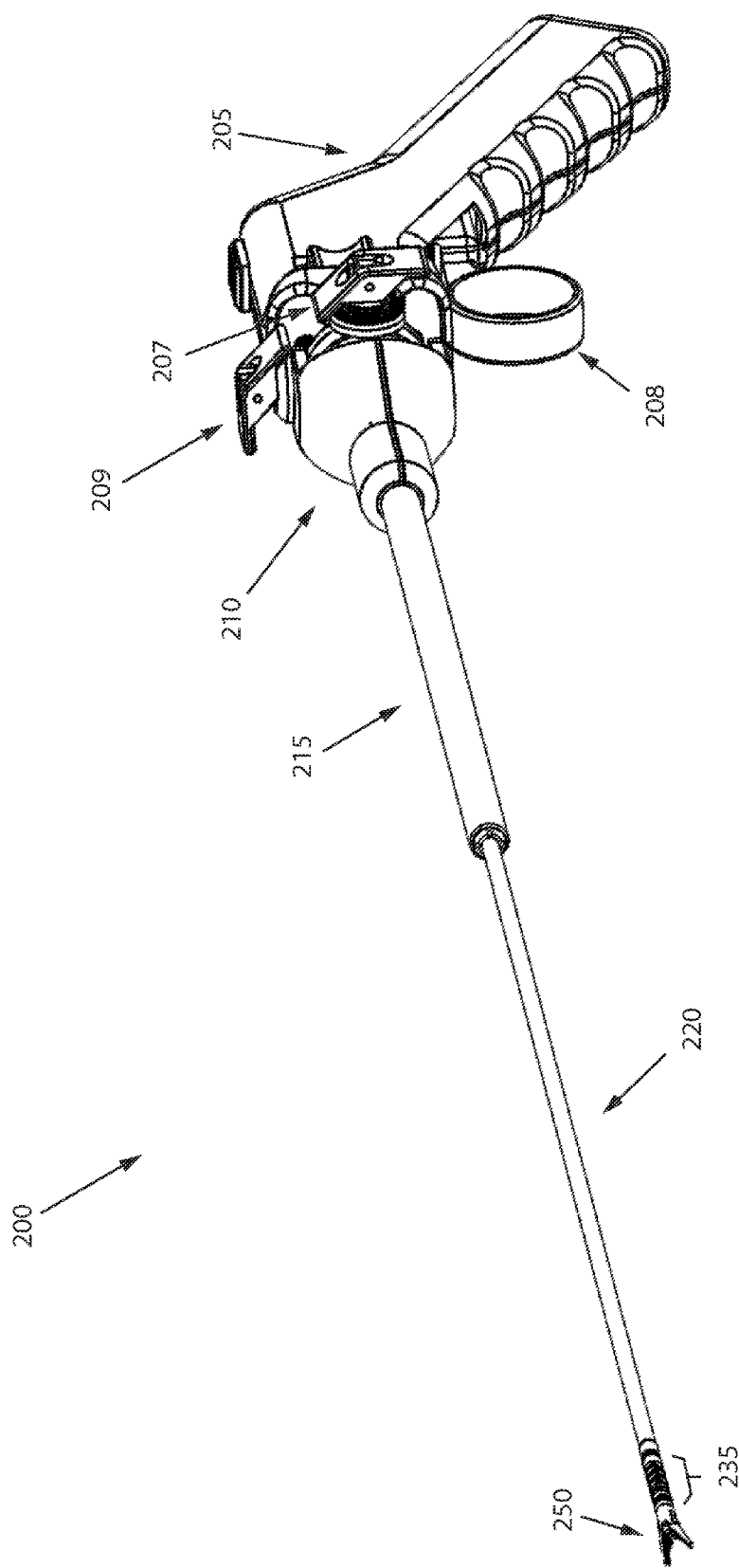
FIG. 1 is a perspective view of an articulating surgical instrument, in accordance with embodiments of the present inventive concepts.

FIG. 1 is a perspective view of an articulating surgical instrument 200, in accordance with embodiments of the present inventive concepts. The surgical instrument 200, also referred to as a surgical tool, can be part of a system for performing a medical procedure, such as a transoral robotic surgery procedure or the like. For example, the instrument 200 can be provided with an articulating robotic probe, for example, slidably positioned within a working channel of the probe and/or a side port or guide hole of an articulating probe, such as the probe described in U.S. Provisional Patent Application No. 61/656,600, now PCT Application No. PCT/US13/43858, filed Jun. 3, 2013, incorporated herein by reference. An operator, such as a medical professional, may manipulate or otherwise control the functions and movement of the surgical instrument 200.

In an embodiment, the surgical instrument 200 includes a handle 205, a housing 210, and an articulation region 235, also referred to as a steerable portion. The surgical instrument 200 can also include a surgical tool shaft that includes a rigid portion 215 and a flexible portion 220, also referred to as flexible tool shaft 220. A proximal end of the rigid portion 215, also referred to as a rigid tool shaft, can be coupled to the tool handle 205, for example, via housing 210 and/or a hub such as the hub 212 shown in FIG. 2. A distal end of the rigid tool shaft 215 can be coupled to a proximal end of the flexible portion 220 of the tool shaft. A distal end of the flexible tool shaft 220 can be directly or indirectly coupled to the articulation region 235. The rigid shaft 215 and the flexible shaft 220 can extend along a same axial direction as the articulation region 235, or a different direction, for example, during movement of the articulation region 235.

Figure 2:
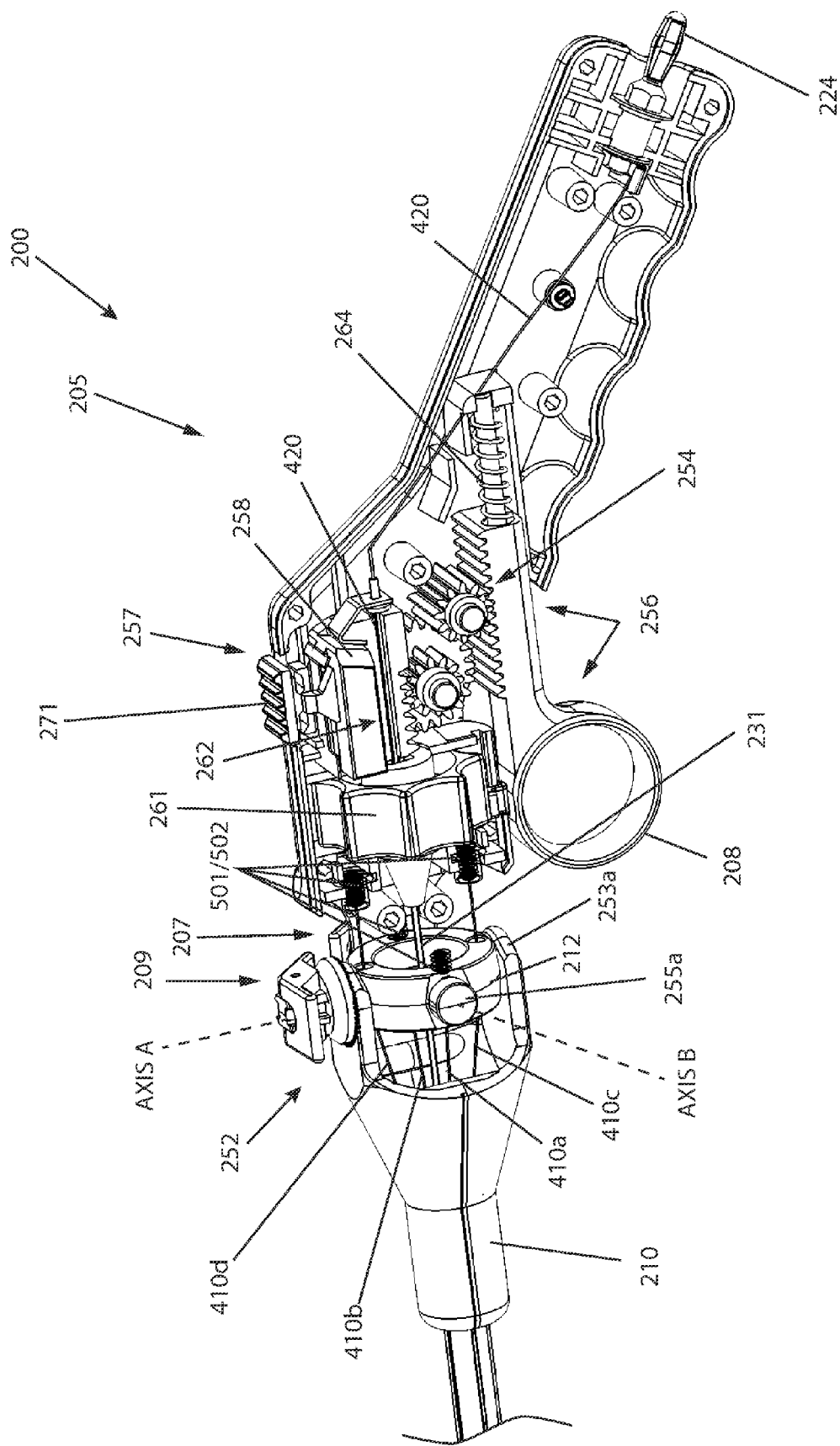
FIG. 2 is a cutaway side view of the surgical instrument of FIG. 1, in accordance with embodiments of the present inventive concepts.

The handle 205 is at a proximal end of the surgical instrument 200, and can be constructed and arranged to control one or more movements of the instrument 200. The handle 205 can be constructed and arranged to include a palm-held grip, a scissors handle, a thumb/index/middle finger grip, a pistol grip, or a reciprocating trigger. The handle 205 includes a plurality of controls that control a movement of the surgical instrument 200, for example, controlling the steering of the articulation region 235, rotating and/or articulating an end effector 250 at a distal end of the surgical instrument 200, and so on. For example, one of the controls at the handle 205 can include a trigger 208 that serves as a ratcheting trigger with respect to the end effector 250, described below. Another control communicates with a power source such as an RF power source via a power source connector 224 as shown in FIG. 2. Another control at the handle can include a control (not shown) in communication with a fluid source, for example, a source of a cooling or washing fluid.

In some embodiments, the rigid portion 215 of the tool shaft includes a rigid tube that is coupled to the housing 210. The rigid tube 215 can surround the proximal end of the flexible shaft 220. The rigid tube 215 can be configured to be slidingly received by a separate support structure to support the instrument 200 and to provide a resistive force during articulation of the handle 205 to enable steering. In some embodiments, the flexible shaft 220 is constructed and arranged to follow a path, for example, a tortuous path, through a working channel of a robotic probe or through a supporting tool guide alongside a robotic probe. These embodiments can be similar to those described in Applicant's co-pending U.S. Non-Provisional application Ser. No. 13/812,324, filed Jan. 25, 2013.

The housing 210 includes a hub 212 (see FIG. 2) that rotatably mates with the handle 205. The handle 205, the housing 210, and the hub 212 communicate with each other in a manner that permits the instrument 200 to provide at least one or two degrees of freedom, for example, to move up and down and/or left to right.

The articulation region 235 is at a distal end of the surgical instrument 200. In other embodiments, the articulation region 235 can be provided at any position between the end effector 250 and the housing 210.

A movement of the handle 205 can provide tension or slack on one or more steering cables, such as steering cables 410 of FIG. 2, thereby adjusting an articulation state of an articulation region 235. An articulation of the handle 205 in accordance with a single degree of freedom can cause the articulation region 235 to move in a single plane or along a single pathway of motion. An articulation of the handle 205 in accordance with two degrees of freedom can permit the articulation region 235 to be manipulated to reach anywhere on a surface of at least a partial sphere. The handle 205 can include locking mechanisms 207 and/or 209, described in detail in FIG. 2 herein and configured to prevent an articulation of the handle in at least one direction. The end effector 250 at the distal end of the surgical instrument 200 can include one or more tools at least partially positioned in a housing. A tool can include but not be limited to a claw, scissors, a cutter, a knife, an ablator, a cauterizer, a drug delivery apparatus, a radiation source such as a laser emitter, an energy delivery element such as a RF or EKG electrode, a sensor such as a pressure sensor or a blood sensor, a camera, a magnet, a heating element, a cryogenic element, or a combination thereof The end effector 250 can relate to the functional elements described with reference at least to PCT Application No. PCT/US12/32279 filed Apr. 5, 2012 and U.S. Provisional Application No. 61/656,600 filed Jun. 7, 2012, now PCT Application No. PCT/US13/43858, filed Jun. 3, 2013, the contents of each being incorporated herein by reference in its entirety. The end effector 250 can be constructed and arranged to articulate between 0° and 180°, or more, with respect to an axis of extension of the tool shaft 215, 220.

FIG. 2 is a side view of the surgical instrument 200 of FIG. 1 with a portion of the handle 205 removed to illustrate inner components. The surgical instrument 200 comprises a U-joint 252 that includes elements of the handle 205, the hub 212, and the housing 210, for providing one or two degrees of freedom between a combination of the handle, the hub, and the housing. Handle 205 is shown in a neutral position (i.e. relative to housing 210), such as a neutral position including a neutral horizontal position and a neutral vertical position such that the articulation region 235 is in a relatively straight orientation (such as is shown in FIG. 6A herebelow). The U-joint includes a first hinge portion 253a at region of the U-joint 252 where a bottom region of the hub 212 is positioned in the housing 210. The U-joint 252 further includes a second hinge portion 253b at a region on the U-joint 252 where a top region of the hub 212 is positioned in the housing 210. The first and second hinge portions 253a and 253b extend within the housing 210 and thus are not shown in FIG. 2, but constructed and arranged to form the first hinge 253. The first hinge 253 can be positioned along the vertical articulating axis A. Accordingly, the first hinge 253 provides a first degree of freedom between the handle 205 and the housing 210, such that the handle 205 can move relative to the housing 210 about the vertical articulating axis A when the vertical locking mechanism 209 is disengaged. For example, the handle 205 can move left and right resulting in a horizontal sweeping motion of the articulation region 235.

The U-joint 252 includes a second hinge 255 along the horizontal articulating axis B, comprising a first hinge portion 255a (shown) and a second hinge portion 255b (not shown). First hinge portion 255a and second hinge portion 255b can have similar construction and arrangement to first and second hinge portions 253a and 253b (both not shown) of hinge 253. The first hinge portion 255a is located at a region on the U-joint 252 where a side region of the hub 212 is positioned within a region of the handle 205 (region of the handle 205 removed to illustrate other instrument 200 components). The second hinge portion 255b (not shown but opposite the first hinge portion 255a) is located at a region on the U-joint 252 where a side region of the hub 212 is positioned within a region of the handle 205. The second hinge 255 is rotatably attached to the handle 205 to provide a first degree of freedom between the hub 212 and the handle 205 such that the handle 205 can move relative to the hub 212 about the horizontal articulating axis B when the horizontal locking mechanism 207 is disengaged. This first degree of freedom between the hub 212 and the handle 205 provides a second degree of freedom between the handle 205 and the housing 210. For example, the handle 205 can move up and down with respect to both the hub 212 and the housing 210, resulting in a vertical motion of the articulation region 235. The U-joint 252 in combination with the locking mechanisms 207 and/or 209 can therefore cause articulation of the handle 205 (e.g. with respect to the housing 210) to occur in any of the four following states: articulation with a single degree of freedom about axis A (i.e. when horizontal locking mechanism 207 is engaged); articulation with a single degree of freedom about axis B (i.e. when vertical locking mechanism 209 is engaged); articulation with two degrees of freedom about axis A and axis B (when neither locking mechanism 207 nor 209 is engaged); and in a locked mode (i.e. prevention of articulation when both locking mechanisms 207 and 209 are engaged). Restricted articulation of the handle 205 causes a corresponding restricted articulation of the articulation region 235. Engagement of the locking mechanisms 207 and/or 209 can therefore permit articulation of the articulation region 235 to occur with either one or two degrees of freedom as described immediately hereabove. Similarly, engagement of the locking mechanisms 207 and 209 can also prevent articulation of the articulation region 235, such as to lock the region 235 in a particular articulated orientation.

When handle 205 is in a vertically neutral position (as shown in FIG. 2) and horizontal locking mechanism 207 is engaged, handle 205 can be articulated in a single plane about axis A, and articulation region 235 will subsequently articulate in a single plane. When handle 205 is in a horizontally neutral position (also as shown in FIG. 2) and vertical locking mechanism 209 is engaged, handle 205 can be articulated in a single plane about axis B, and articulation region 235 will subsequently articulate in a single plane.

The controls in the handle 205 can advance and/or retract a plurality of steering cables 410a-410d (generally, 410), also referred to as articulation cables, coupled between a proximal portion of the tool 200 and the distal end of the articulation region 235. Articulation region 235 can articulate in either a single degree of freedom steering mode or a multiple degree of freedom steering mode as described hereabove. One or more steering cables 410 can extend from the U-joint 252 through a path extending through the housing 210 and the tool shaft 215, 220 to the distal end of articulation region 235. Steering cables 410a, 410b can be constructed and arranged as horizontal steering cables, which extend from the hub 212 to the articulation region 235, and when activated move the articulation region 235 with a single degree of freedom (e.g. in a single plane when handle 205 is in the vertically neutral position shown or otherwise along a single pathway). The steering cables 410a, 410b can fixedly attach to the hub 212 at attachment points 501a, 501b, respectively. Attachment points 501a, 501b can be positioned along axis B, within the hub 212, such that articulation of the hub 212 with respect to the housing 210 (i.e. via horizontal articulation of the handle 205) causes a movement of the cables 410a, 410b. Articulation of the handle 205 to the left causes hub 212 to articulate counter clockwise about axis A, "pulling" cable 410a, and allowing cable 410b to "feed" into the housing 210. This motion of the cables 410a, 410b causes the articulation region 235 to articulate to the left, as described in FIGS. 6 and 7 herebelow.

Steering cables 410c and 410d can be constructed and arranged as vertical steering cables, which extend from the handle 205 to the articulation region 235, and when activated move the articulation region 235 with a single degree of freedom (e.g. in a single plane when handle 205 is in a horizontally neutral position shown or otherwise along a single pathway). The steering cables 410c, 410d can fixedly attach to the handle 205 at attachment points 501c, 501d, respectively. When U-joint 252 is in a relatively neutral orientation, attachment points 501c, 501d can be positioned within the handle 205 such that steering cables 410c, 410d are aligned with through-holes, for example through-holes 443b, 443a detailed in FIG. 4, respectively. Articulation of the handle 205 with respect to the hub 212 (i.e. via vertical articulation of the handle 205) causes a movement of the cables 410c, 410d. For example, articulation of the handle 205 in an upward direction causes the handle 205 to articulate counter clockwise about axis B, "pulling" the cable 410c, and allowing the cable 410d to "feed" into the housing 210 via the through-hole 443a. This motion of the cables 410c, 410d causes the articulation region 235 to articulate downwards, as described in FIGS. 6 and 7 herebelow.

The handle 205 and/or hub 212 can include a cable tensioning mechanism 502 that secures the proximal ends of the steering cables 410. The cable tensioning mechanism 502 allows for the manufacture and adjustment of the tension within the cable system, described further in FIG. 5 herebelow.

The articulation region 235 can move in a single plane of motion, for example, a vertical plane, in response to a movement of at least one of the steering cables 410c, 410d in a direction between the handle 205 and the distal end of articulation region 235. A movement of the at least one of the steering cables 410c, 410d along a plane relative to the horizontal axis B can occur in response to a movement by the handle 205 relative to the housing 210 in a second degree of freedom that is different than, for example, orthogonal to, the first degree of freedom, and that can be provided between the hub 212 and the handle 205 at the second hinge 255 of the U-joint 252. The articulation region 235 can move in the single plane of motion in response to a movement of at least one of the third or fourth steering cables 410c, d in an axial direction between the handle 205 and the articulation region 235.

The surgical instrument 200 can include a support element 231 having a proximal end coupled to the handle 205 and a distal end coupled to a housing (e.g. a clevis) or related device at or proximal to the end effector 250. The support element 231 can be constructed and arranged to rotate independently of the movement of the articulation region 235 with a single degree of freedom (e.g. to cause an axial rotation of end effector 250). The support element 231 can include elastic bending and/or plastic deformation characteristics, and can therefore flex or bend in response to a flexing or bending of the shaft 220 and/or the articulation region 235. The support element 231 can be constructed and arranged as a coil, rod, hollow tube, or related structure. The support element 231 can have a cross-section of any well-known suitable shape, including but not limited to a circle, oval, polygon, square, triangle, or a rectangle. The support element 231 includes a lumen that extends along a direction of extension of the support element 231. One or more devices can be advanced through the lumen of support element 231, such as a laser fiber, tip-electrode device or other flexible device that can be subsequently positioned and/or manipulated by tool 200. In some embodiments, the inserted tool is an electrically powered device that is electrically isolated from support element 231 and/or other components of tool 200. Alternatively, an activation element 420 can be positioned in the lumen, and can move relative to the support element 231, for example, along the direction of extension of the support element 231. A proximal end of the activation element 420 can be coupled to a translating assembly 258. A distal end of the activation element 420 can be coupled to the end effector 250 to activate the end effector 250. Accordingly, a movement of the activation element 420 can be induced at the handle 205. The activation element 420 can be constructed and arranged as a metal cable, a plastic cable, a sold wire cable, a braided cable, a stainless steel wire braided cable, an electrical conduit, or the like.

Forces related to tension, slack, and the like can be applied by the activation element 420 in response to a movement of a component of the handle 205, for example, squeezing the trigger 208. In one embodiment, the activation element 420 moves freely within the support element 231. In another embodiment, the activation element 420 can move freely proximal to an outer surface of the support element 231. The activation element 420 can be coupled to the trigger 208 via the translating assembly 258. The trigger 208 can be spring-loaded, for example, including a spring assembly. The trigger 208 when pulled or otherwise activated can induce a motion of the activation element 420. In particular, the activation element 420 can move in a direction towards the handle assembly 205. A release of the trigger 208 by an operator causes the trigger 208 to reset in turn allowing the activation element 420 to move in an opposite direction, for example, toward the end effector 250.

For example, the end effector 250 can include an actuating piston or the like (not shown) coupled between claw members or grasper members of the end effector 250 which open and close in response to a tension applied to an actuating element 420 coupled to the actuating piston. In some embodiments, the actuating piston can comprise an actuating piston as described in U.S. Provisional Application No. 61/656,600, filed Jun. 7, 2012, now PCT Application No. PCT/US13/43858, filed Jun. 3, 2013, the content of each being incorporated herein by reference in its entirety.

The handle 205 includes the horizontal locking mechanism 207 and/or the vertical locking mechanism 209, each for enabling and disabling a degree of freedom in motion of handle 205 and a corresponding degree of freedom in motion of articulation region 235. Each locking mechanism 207 and 209 can be controlled by one or more locking controls (e.g. a locking cam). The horizontal locking mechanism 207 and/or vertical locking mechanism 209, when activated, can prevent the steering mechanism from articulating with one or two degrees of freedom, which in turn can limit the articulation region 235 to movement with a single degree of freedom (when one of locking mechanism 207 or 209 is activated), or prevent any articulation of the articulation region 235 (when both locking mechanisms 207 and 209 are activated). For example, the vertical lock 209, when engaged, can limit the U-joint 252 to prevent a first degree of motion, (e.g. left/right motion) of the articulation region 235. Here, the housing 210 and shaft 215, 220 are prevented from rotating about a vertical articulating axis A relative to the hub 212 and the handle 205. Although the articulating axis A is referred to as a vertical articulating axis, in other embodiments, the articulating axis A extends in a direction other than a vertical axis. As a result, when the vertical lock 209 is engaged, and the horizontal lock 207 is disengaged, the articulation region 235 can articulate with a single degree of freedom, for example, up and down.

The horizontal lock 207, when engaged, can disable a second degree of motion (e.g. up/down motion) of the articulation region 235. Here, the handle 205 is prevented from rotating about a horizontal articulating axis B relative to the hub 212, the housing 210, and shaft 215, 220. Although the articulating axis B is referred to as a vertical articulating axis, in other embodiments, the articulating axis B extends in a direction other than a horizontal axis. As a result, the articulation region 235 can articulate with a single degree of freedom, for example, left to right. The motion permitted when the horizontal lock 207 is disabled can be orthogonal to the motion permitted when the vertical lock 209 is disabled (e.g. two orthogonal planes of motion). When both the horizontal lock 207 and the vertical lock 209 are disengaged, the articulation region 235 can articulate with multiple degrees of freedom (e.g. in multiple planes of motion). Here, when neither locking mechanism 207, 209 is engaged, an articulation of the handle 205 in accordance with two degrees of freedom can permit the articulation region 235 to be manipulated to reach anywhere on a surface of at least a partial sphere.

Tool 200 can be constructed and arranged such that handle 205 is articulated away from a neutral position, after which one of locking mechanisms 207, 209 are engaged (i.e. articulation region 235 is locked in a curvilinear orientation). Subsequent articulation of handle 205 relative to housing 210 causes articulation region 235 to travel along a curvilinear path with a single degree of freedom (e.g. each segment of articulation 235 sweeps along an arc).

The ratchet mechanism 257 in the handle 205 can be constructed and arranged to maintain the translating assembly 258 in a series of linear positions. In doing so, the translating assembly 258 can slide back and forth in the handle 205, and can advance and retract the activation element 420 with respect to the support element 231. The translating assembly 258 can be controlled by the trigger assembly 256, for example, by squeezing the trigger 208, causing the linear translation of the translating assembly 258, which in turn applies a force at the activation element 420.

The ratchet mechanism 257 can be configured to, when engaged in a step-wise incremental fashion, resist the force of a trigger spring 264, and maintain the translating assembly 258 in a series of linear positions. The ratchet mechanism 257 includes a ratchet selector 271 that is constructed to be temporarily disengaged, for example, by an operator, to release the translating assembly 258, or to be locked in a disengaged position such that the trigger 208 only (i.e. no ratcheting) controls the translating assembly 258. Activation and de-activation of the ratchet mechanism 257 is achieved by moving the ratchet selector 271, as is described in detail in reference to FIG. 3 herebelow.

Figure 3:
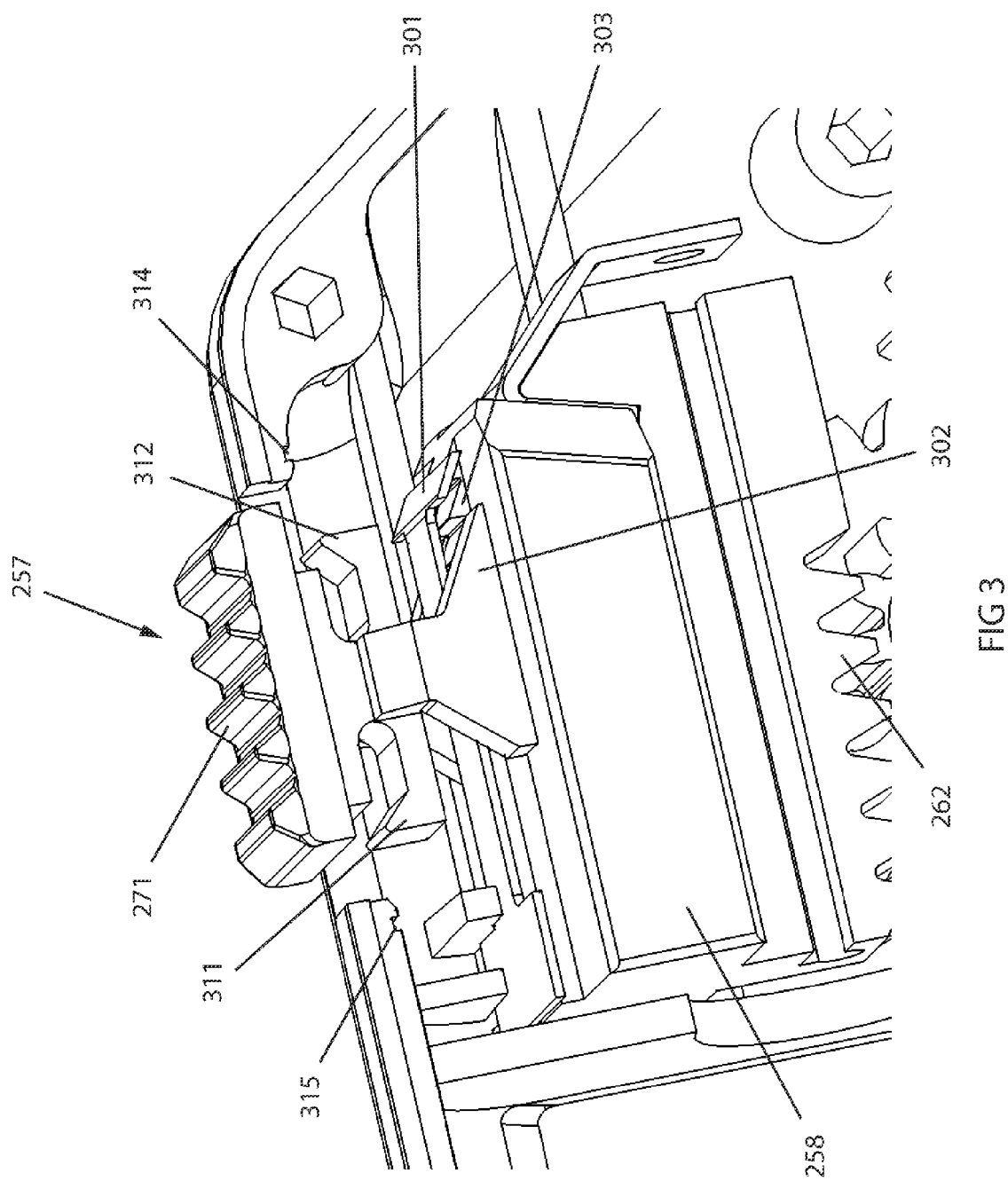
FIG. 3 is a close-up view of the ratchet mechanism and translating assembly of the surgical instrument of FIGS. 1 and 2, in accordance with embodiments of the present inventive concepts.

FIG. 3 is a close-up view of the ratcheting mechanism 257 and translating assembly 258 of the surgical instrument 200 of FIGS. 1 and 2, in accordance with embodiments of the present inventive concepts. The activation element 420 has been removed for illustrative clarity.

The ratchet mechanism 257 can comprise a ratchet lock 301, a release ramp 302, and the ratchet selector 271 configured to move the ratchet lock 301 to a position for engaging or disengaging with the translating assembly 258.

The translating assembly 258 comprises a plurality of ratchet teeth 303. In a first, engaged position, the ratchet lock 301 can sequentially engage, e.g., through flexing such as when comprising a flexible plastic material or thin metal, the ratchet teeth 303 of the translating assembly 258 as it moves proximally. A distal movement of the translating assembly 258 is prevented while the ratchet lock 301 is engaged with the ratchet teeth 303. Sizing of the ratchet teeth 303 can be established to determine a "step size" of lockable movement. In a second, disengaged position, the release ramp 302 slides beneath the ratchet lock 301 and disengages the lock 301 from the ratchet teeth 303, allowing the translating assembly 258 to move freely.

As shown, the translating assembly 258 can be at distalmost position, and the ratchet selector 271 can be at an intermediate "open" position, i.e. not yet engaged or disengaged. The ratchet selector 271 can include a first securing projection 311 and a second securing projection 312. The handle 205 includes a housing having a first notch 315 and a second notch 314 that frictionally engages with the first 311 and second securing projection 312, respectively.

When the ratchet selector 271 is slid distally, the first securing projection 311 can frictionally engage the first notch 315 in the handle housing, thereby locking the ratchet selector 271 in the "engaged on" position so that the ratchet is engaged. When the selector 271 is slid proximally, the second securing projection 312 frictionally engages the second notch 314 in the handle housing, thereby locking the ratchet selector 271 in a "disengaged off" position. In the disengaged off position, the release ramp 302 slides beneath the ratchet lock 301, lifting the lock 301 off the ratchet teeth 303 of the translating assembly 258, thereby releasing the ratchet and allowing the translating assembly 258 to move freely, e.g. not in discrete steps, in proximal or distal directions as determined by the position of the trigger 208.

Returning to FIG. 2, the translating assembly 258 is translated via the gearing mechanism 254 attached to the trigger assembly 256. The translating assembly 258 comprises a linear gear 262 that mates with the gearing mechanism 254, such that gearing mechanism 254 can drive the translating assembly 258 proximally and distally within the handle 205. As described herein, the translating assembly 258 can advance and retract the activation element 420. The gearing mechanism 254 can be configured to provide a division of travel distance between the translating assembly 258, which can allow for finer control, or less movement per trigger travel, of the end effector 250 and/or an application of higher force. Alternatively, the gearing mechanism 254 can be configured to increase a travel distance, for example, a multiplication of travel distance, for gross control, or more movement per trigger travel, of the end effector 250 and/or an application of lower force, e.g. to limit forces applied by the end effector 250.

The handle 205 can further comprise a rotation knob 261 coupled to the support element 231, and that provides a rotational force to the support element 231, which in turn can rotate the end effector 250 coupled to the distal end of the support element 231.

The trigger assembly 256 comprises a trigger 208 and a spring 264 which is biased to maintain the trigger 208 in a position. The trigger 208 can be in an un-pulled position, such as in a position in which the end effector 250 is in an open or un-activated position. The ratchet mechanism 257 can be constructed and arranged to resist the force of the trigger spring 264. As described herein, the ratchet mechanism 257 can be constructed to be temporarily disengaged to release the translating assembly 258, or to be locked in a disengaged position such that the trigger 208 controls the translating assembly 258. As also described herein, the ratchet selector control 271 can be moved to a position for activating and/or de-activating the ratchet mechanism 257.

FIG. 4 is a cutaway close-up view of the locking mechanisms 207 and 209 and the U-joint 252 of the surgical instrument 200, in accordance with embodiments of the present inventive concepts. The handle 205 has been removed for illustrative clarity.

The hub 212 includes a first clamp post 402. The first clamp post 402 extends vertically from the hinge portion 253b (not shown but opposite the hinge portion 253a) through an opening (not shown) in a portion of the housing 210 along vertical axis A.

The vertical lock 209 can include a clamping mechanism comprising a locking ring 411 and a cam clamp 412 in communication with the first clamp post 402. The cam clamp 412 is positioned on the first clamp post 402. The locking ring 411 is slidingly received by the clamp post 402, via an opening, configured such that the locking ring 411 cannot rotate about the clamp post 402. The locking ring 411 can include a set of interdigitating teeth 414. During a locking operation, the cam clamp 412 can apply a force to the locking ring 411 and therefore press the locking ring 411 towards the housing 210, locking the teeth 414, for example, so that the teeth 414 are pressed against an opposing set of teeth coupled to a surface 211 of the housing 210, to prevent a rotation of the housing 210 with respect to the hub 212 about the vertical articulating axis A.

When the hub 212 is locked in this manner, the housing 210 and a shaft region coupled between the housing 210 and the articulation region 235 are locked in a fixed orientation, such that horizontal steering cables 410a, 410b are locked in a fixed orientation with respect to articulation region 235, locking the horizontal articulation position of articulation region 235. Accordingly, an isolated vertical control of the articulation region 235 can be achieved, or a control of an articulation comprising only a change to the vertical component of the position of the distal tip of the articulation region 235. In a released position, the mating force between the teeth 414 of the locking ring 411 and the teeth of the surface 211 is removed, allowing the teeth 414 to rotatably slide with respect to the opposing teeth or otherwise preventing locking.

The hub 212 includes a second clamp post 422. The second clamp post 422 extends horizontally from hinge portion 255b through an opening (not shown) in a portion of the housing 210 along horizontal axis B. The horizontal lock 207 can include a clamping mechanism comprising a locking ring 430 and a cam clamp 432 in communication with the second clamp post 422. The cam clamp 432 is positioned on the second clamp post 422. The locking ring 430 is slidingly received by the clamp post 422, via a shaped opening, such that the locking ring 430 cannot rotate about the clamp post 422. The locking ring 430 can include a set of interdigitating teeth 434. During a locking operation, the cam clamp 432 can apply a force to the locking ring 430 and therefore press the locking ring 430 towards the handle 205, locking the teeth 434, for example, so that the teeth 434 are pressed against an opposing set of teeth (not shown) coupled to the handle 205, to prevent a rotation of the handle 205 about the horizontal articulating axis B.

When the hub 212 is locked in this manner, the handle 205 (not shown) and the hub 212 are locked in a fixed orientation, such that the vertical steering cables 410c, 410d are locked in a fixed orientation with respect to articulation region 235, thus locking the vertical articulation position of the articulation region 235. Accordingly, an isolated horizontal control of the articulation region 235 can be achieved, or a control of an articulation comprising only a change to the horizontal component of the position of the distal tip of the articulation region 235. In a released position, the mating force between the teeth 434 of the locking ring 430 and the handle is removed, allowing the teeth 434 to rotatably slide with respect to the opposing teeth or otherwise prevent locking.

Accordingly, activation of either the vertical lock 209 or the horizontal lock 207 limits movement of the articulation region 235 to a single degree of freedom motion (e.g. motion in a single plane). Also, activation of both the vertical lock 209 and the horizontal lock 207 prevents steering of the instrument 200, and maintains an end effector at a distal end of the instrument tool 200, in particular, at the end of the articulation region 235, in a current position.

The hub 212 can include cable fastening locations 442a, 442b that couple proximal ends of the horizontal steering cables 410a, 410b, respectively, to the hub 212. Steering cables 410c, 410d shown in FIG. 2 can be constructed and arranged as vertical steering cables. Proximal ends of the steering cables 410c, 410d extend through the pass-through holes 443a, 443b, respectively, in the hub 212 to the handle 205.

The position of fastening locations 442a, 442b relative to axis A provide a mechanical advantage that determines the scale and/or fidelity of the motion of cables 410a, 410b, respectively, corresponding to articulation of hub 212 relative to housing 210. In other words, the greater the distance from axis A to fastening locations 442a, 442b, the greater the motion of cables 410a, 410b per angular displacement of hub 212 relative to housing 210. Correspondingly, a decrease in the distance from axis A to fastening locations 442a, 442b, results in finer control of (and increase force applied to) cables 410a, 410b. Similarly, as depicted in FIG. 2, locations of attachment of cables 410c, 410d can be manipulated to adjust scale, fidelity and applied force that occurs during articulation of handle 205 relative to hub 212.

Figure 5C:
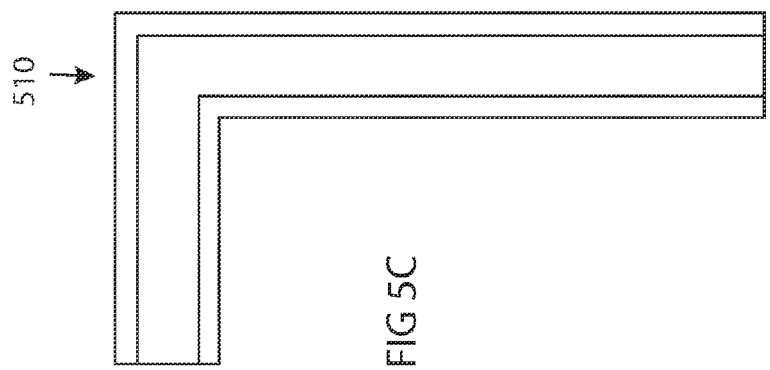
FIG. 5C is a side view of a tool used for adjusting a cable tension, in accordance with an embodiment.
Figure 5A:
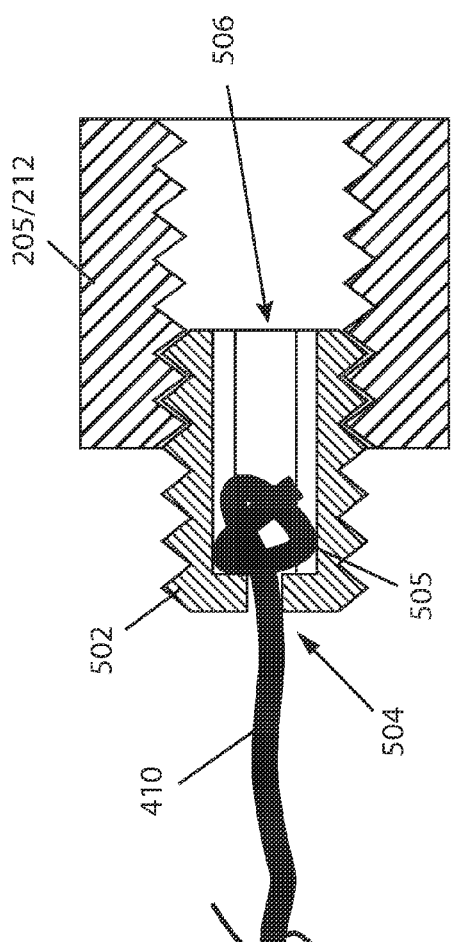
FIGS. 5A and 5B are cutaway side views of a cable tensioning mechanism, in accordance with an embodiment.
Figure 5B:
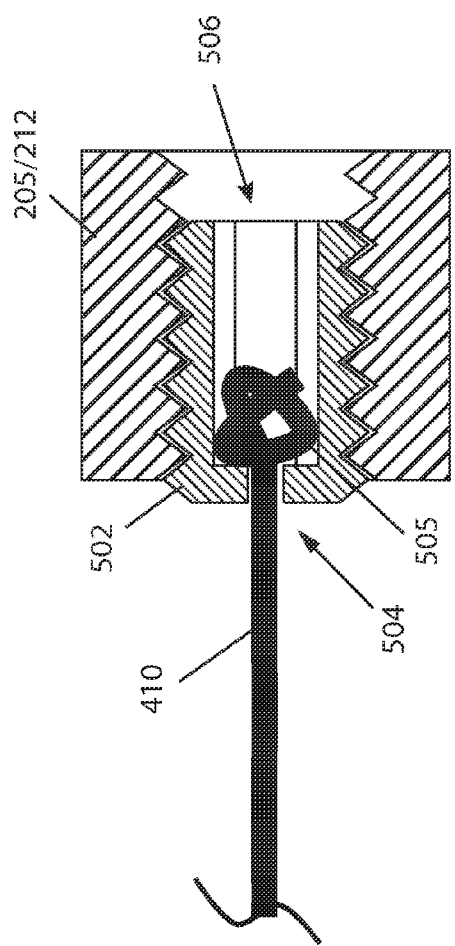

FIGS. 5A and 5B are cutaway side views of a cable tensioning mechanism 504, in accordance with an embodiment. FIG. 5C is a side view of a tool 510 used for adjusting a cable tension, in accordance with an embodiment.

As shown in FIGS. 2 and 4, the proximal ends of the vertical steering cables 410c, 410d can extend through pass through holes 443a, 443b, respectively, in the hub 212 to a region of the handle 205 proximal to the hub 212. The proximal ends of the horizontal steering cables 410a, 410b terminate at cable fastening locations 442a, 442b, respectively, at the hub 212. The handle 205 and/or hub 212 can include a cable tensioning mechanism 502 that secures the proximal ends of the steering cables 410. The cable tensioning mechanism 502 allows for the manufacture and adjustment of the tension within the cable system, such as to increase the sensitivity of motion of articulation region 235, such as an increase in the initial articulation from a linear configuration. The tensioning mechanism 502 can comprise set screws or the like configured to slidingly receive the proximal end 505 of the cable 410, which can be secured to the set screw via a knot, crimp, or other means of insuring the cable does not release from the distal opening of the set screw (knot shown). The set screws or the like can be threaded in sockets 506 in the handle 205 and/or the hub 212 to adjust the tension.

FIG. 5A illustrates a steering cable 410 coupled to a cable tensioning mechanism 502 prior to tightening (e.g. threading into the handle 205 or hub 212), and FIG. 5B illustrates the steering cable 410 after tightening. The steering cables 410 are configured to rotate freely within the tensioning mechanisms 502 such that the cables 410 do not twist or wind up as tensioning mechanisms 502 are secured into the sockets 506. A tool 510, such as an alien wrench, can be used to tighten the tensioning mechanisms 502 via proximal access to the sockets 506. The tensioning mechanisms 502 can be tightened until the proper tension is achieved in each steering cable 410. This can be performed with a torque or a slip wrench, as to eliminate human or user error from the manufacture or adjustment process.

Figure 6C:
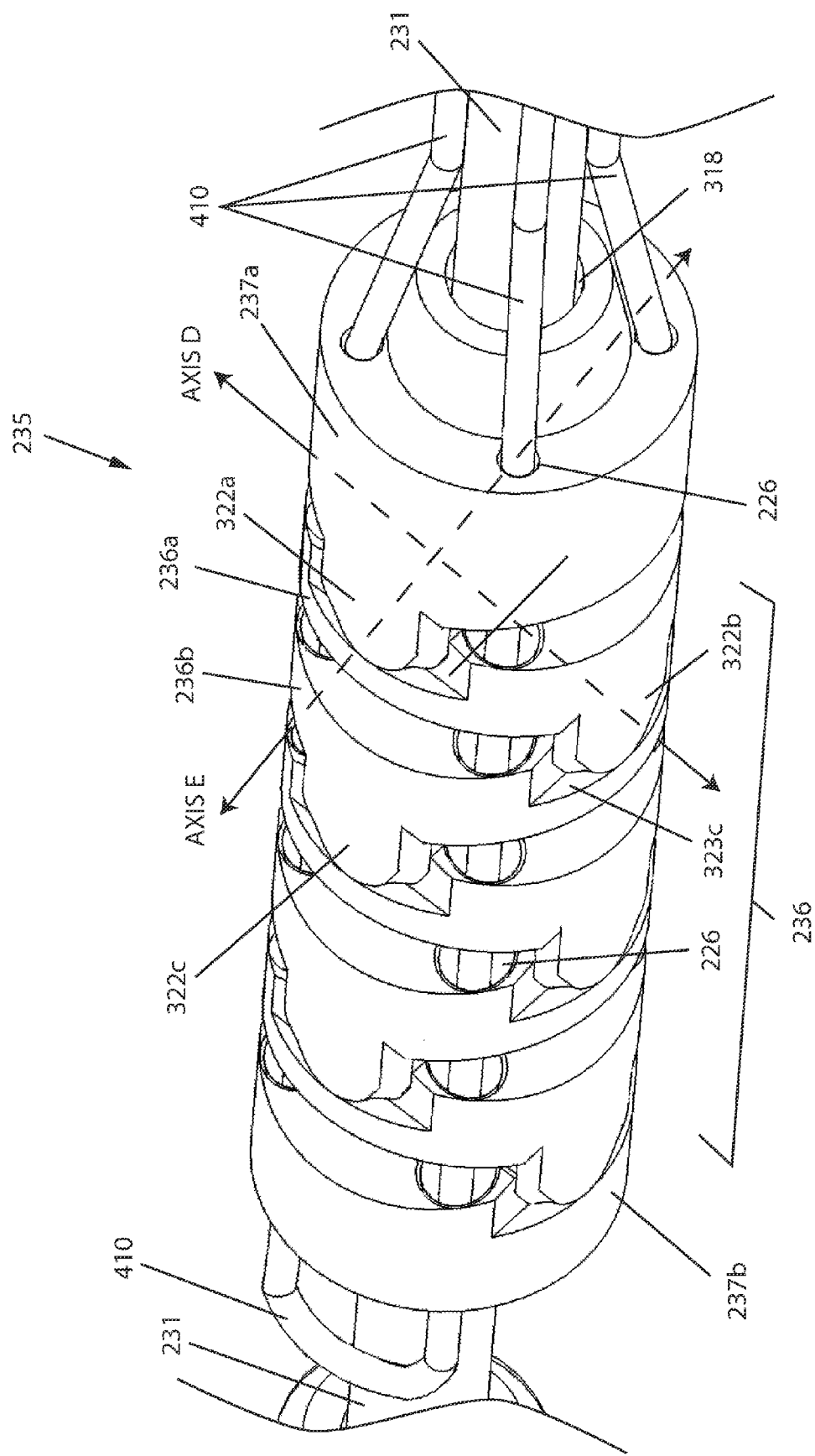
FIG. 6C is a close-up perspective view of articulation region of the surgical instrument of FIGS. 1-6B.
Figure 6D:
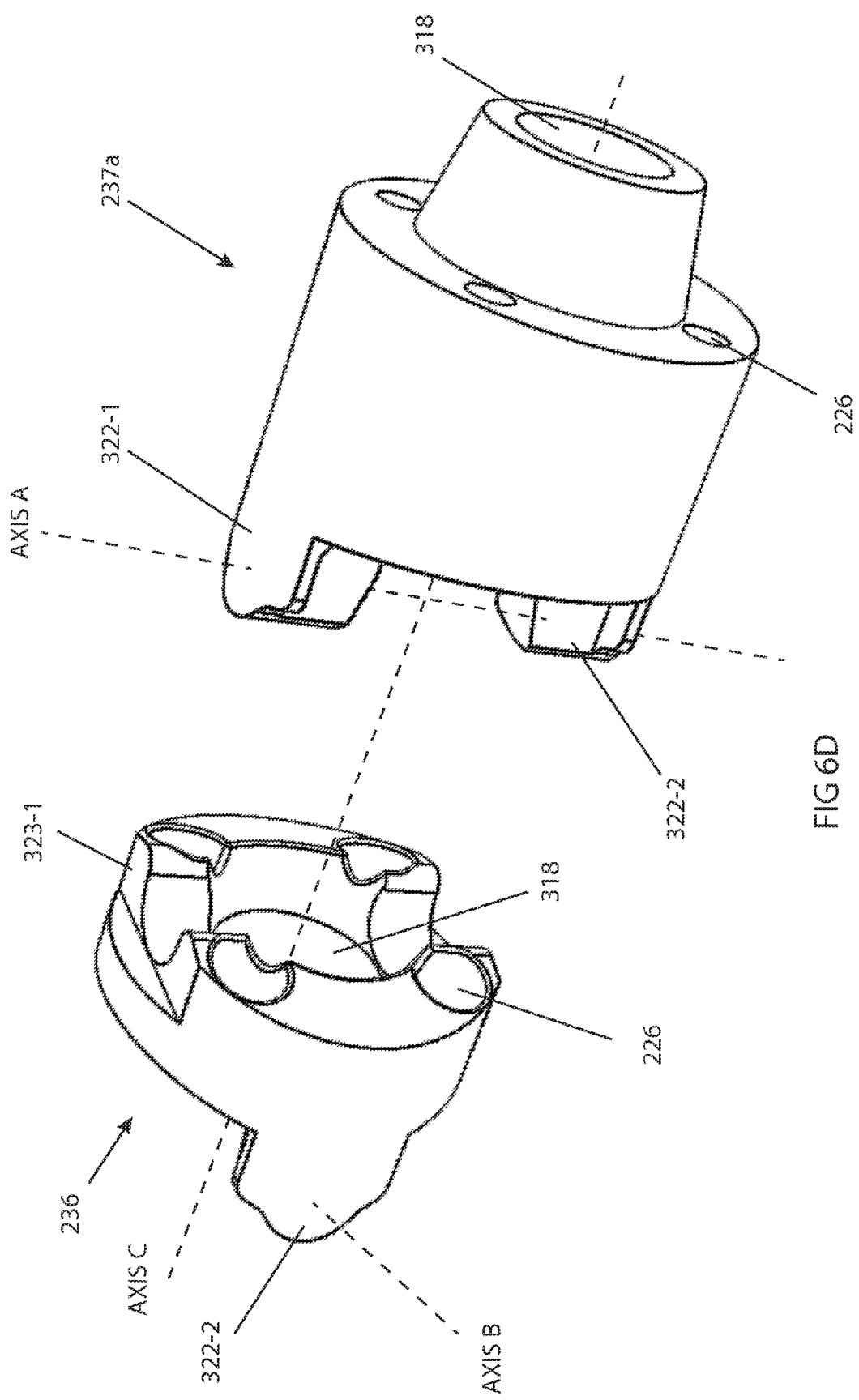
FIG. 6D is a close-up perspective view of two adjacent segment links of FIGS. 1-6C, in accordance with an embodiment.

FIGS. 6A and 6B are perspective views of a distal end of the surgical instrument 200 of FIGS. 1-5. FIG. 6C is a close-up perspective view of an articulation region 235 of the surgical instrument 200 of FIGS. 1-6B. FIG. 6D is a close-up perspective view of two adjacent segment links 236, 237 of FIGS. 1-6C, in accordance with an embodiment.

Articulation region 235 is shown in a relatively straight orientation, such as when handle 205 is in a neutral position relative to housing 210, such as a neutral position including a neutral horizontal position and a neutral vertical position of handle 205 relative to housing 210. The articulation region 235 can include a proximal segment 602, a distal segment 604, and at least three segment links 236, 237 between the proximal segment 602 and the distal segment 604.

The proximal segment 602 is positioned between the flexible shaft 220 and a first end link 237a of the segment links 236, 237. At least a portion of the flexible shaft 220 is directly or indirectly coupled at the proximal segment 602. The proximal segment 602 can include a cable transitioning segment, which distributes one or more actuating cables and/or one or more articulation cables, from the tool shaft 215, 220 to through channels 226 of the segment links 236, 237, respectively.

The distal segment 604 is positioned between the end effector 250 and a second end link 237b of the segment links 236, 237. The distal segment 604 can be coupled to the end effector 250. For example, the distal segment 604 can be coupled to a housing 251 of the end effector 250. Distal segment 604 can be configured to slidingly receive the housing 251 such that the end effector 250 can freely rotate with respect to the distal segment 604, and thus the articulation region 235. In other embodiments, as described above, the articulation region 235 is provided at any position between the end effector 250 and a proximal end of the tool shaft 215, 220. For example, a first segment link 236, 237 can be coupled directly or indirectly to a first region of the tool shaft 215, 220, and a second segment link 236, 237 can be coupled directly or indirectly to a second region of the tool shaft 215, 220.

The steering cables 410 can extend through a lumen in the flexible shaft 220, along with the support element 231. FIG. 6B illustrates the steering cables 410 and the support element 231 by the removal of the outer tubular portion of the flexible shaft 220 and the proximal segment 602. At the proximal segment 602, the steering cables 410 are directed into channels 226, or thru holes, of the first end link 237a, thru holes 226 of one or more segment links 236, and/or thru holes 226 of the second end link 237b. The steering cables 410 can terminate at the distal segment 604 (also removed for illustrative purposes). In some embodiments, a single physical cable can be employed to provide two steering cables 410, for example, two adjacent steering cables 90 degrees apart, wherein the cable is looped around a portion of the second end link 237b and/or distal segment 604, and at least secured on both cable ends positioned within the proximal end of the tool (i.e. the cables 410a and 410b of FIG. 2 can comprise a single, looped cable).

The support element 231 can extend along a length of the flexible shaft 220, through a central working channel 318 formed by one or more holes or through a central region of each link 236, 237 of the articulation region 235, and can terminate at a housing 251 of the end effector 250. Rotation of the support element 231, for example, by rotation of the knob 261, can cause the end effector 250 to rotate. A rotation in this manner can be achieved independently of an orientation of the articulation region 235.

The segment links include a first end link 237a, a second end link 237b, and at least one central link 236 between the first end link 237a and the second end link 237b. The segment links 236, 237 are constructed and arranged to articulate relative to each other based on forces applied to the steering cables 410, for example, which are controlled by the handle 205 and articulate the articulation region 235 in response to the forces. Each segment link 236, 237 has a single degree of freedom with respect to each adjacent segment link 236, 237.

The segment links 236, 237 can each be unitary in form, or can each be constructed of multiple portions of material that are bonded or coupled together. Each segment link 236, 237 includes a central hole, working channel 318 positioned along a central axis C and a plurality of holes 226, or cable channels, positioned about a periphery of the segment link 236 and extending along an axis parallel to the central axis. The holes 226 can include four holes that are 90 degrees apart from each other about the central axis C. In another embodiment, the holes 226 include two holes that are 180 degrees apart from each other. The central axis C of the segment links 236, 327 can be the same, as shown in FIG. 6C. As shown in FIGS. 7A-7E, the central axes C, C', C'', and so on of the segment links 236, 237 can be different. When the articulation region 235 articulates with a single degree of freedom (e.g. in a single plane of motion), each pair P1-P4 of adjacent links 236, 237 can extend along a different central axis, while each link 236, 237 in a pair P1-P4 can extend along a same central axis. A steering cable 410 can extend through each periphery hole 226. Each steering cable 410 has a distal end that terminates at the second end link 237b, or other distal segment 236.

The steering cables 410 include at least one horizontal steering cable extending through a first hole 226 in one or more segment links 236, 237, and at least one vertical steering cable extending through a second hole 226 in one or more segment links 236, 237. The horizontal cable 410 can be constructed and arranged to move the articulation region 235 in along a horizontal plane. The vertical cable can be constructed and arranged to move the articulation region 235 in along a vertical plane.

As described herein, three segment links 236, 237 adjacent to each other are constructed and arranged to have two degrees of freedom, and any two adjacent segment links 236, 237 are constructed and arranged to have a single degree of freedom, which can translate to a movement of the articulation region 235 in a single degree of freedom steering mode or a multiple degree of freedom steering mode, depending on the configuration of the handle controls, for example, which can lock the steering mechanism in one or more steering modes.

A segment link 236 has a projection, protrusion 322, extending from one side of the segment link 236 and a slot 323 at an opposite side of the segment link 236, and orthogonal to the protrusion 322. Either or both sides of the segment link 236 can be convex, concave, semi-ellipsoidal, semi-spherical, or related configuration. To provide one or two degrees of freedom described herein, the protrusion 322 of the segment link 236 is orgothonal to a protrusion 322 of an adjacent segment link 236 or end link 237, and the slot 323 of the segment link 236 is orgothonal to a slot 323 of an adjacent segment link 236 or end link 237.

The first end link 237a has a protrusion 322 and no slot. The second end link 237b has a slot 323 and no protrusion.

As illustrated in FIG. 6C, the articulation region 235 can include a protrusion 322a of a first link, for example, end link 237a or a segment link 236, which extends along a first axis E, and the protrusion 322b of a second link 236a adjacent the first link 237a, which extends along a second axis D that is orthogonal to the first axis E. In this configuration the slot 323b in the second link 236a also extends along the first axis E for mating with the protrusion 322a of the first link 237a. The second link 236a can have a protrusion 322b which mates with a slot 323c of an adjacent third link 236b along the second axis D. The slots 323 of the links 236 each have a length along which a protrusion 322 can be positioned, and can slidingly engage with a slot 323 along its length during rotation about an axis E or D. A link 236, 237 can rotate about an axis E or D subject to the length of the slot 323 of the adjacent link 236, 237 in which the protrusion 322 of the rotating link is positioned. An angle of articulation between adjacent links 236, 237 can be determined, for example, restricted, by the length of the slot 323 and/or width of the protrusion 322 mating with the slot 323. Each link 236, 237 only moves with a single degree of freedom with respect to each adjacent link 236, 237 to prevent an undesired rotation of the links 236, 237 (e.g. about central axis C).

The three segment links, e.g., first link 237a, second link 236a, and third link 236b, are constructed and arranged to have two degrees of freedom with respect to a movement. Any adjacent pair of segment links, for example, first link 237a and a second link 236a, or second link 236b and a third link 236b, are constructed and arranged to have a single degree of freedom with respect to a movement. In doing so, one segment link, for example, second link 236a at least partially rotates about the first axis E. Here, the slot 323b of the second link 236a and the mating protrusion 322a of the first end link 237a move relative to each other to provide a single degree of freedom. Also, the protrusion 322b of the second link 236a and the slot 323c of the third link 236b move relative to each other to provide a single degree of freedom. Alternating segment links, for example, links 237a and 236b shown in FIG. 6C, each have protrusions, for example, 322a and 322c, respectively, that extend along a same axis, and/or slots that extend along a same axis, which is orthogonal to the axis along which their protrusions extend. The combination of these movements of the first link 237a, second link 236a, and third link 236b can therefore provide two degrees of freedom.

As shown in FIG. 6D, each segment link 236 and the first end link 237a can include a first protrusion 322-1 and a second protrusion 322-2 at 180 degrees relative to the first protrusion 322-1, and extending along a first axis A orthogonal to the links' central axis C. The segment links 236 and the second end link 237b (see FIG. 6C) can include a first slot 323-1 and a second slot 323-2 at 180 degrees relative to the first slot 323-1, and extending along a second axis B orthogonal to the first axis A. Each slot 323-1, 323-2 is positioned 90 degrees from each protrusion 322-1, 322-2. Each protrusion 322-1, 322-2 is constructed and arranged to mate with a slot 323-1, 323-2 at an adjacent segment link 236, 237b to provide a first degree of freedom about the first axis A. The slots 323-1, 323-2 are opposite and perpendicular to the protrusions 323-1, 323-2 of the link 236, such that the protrusions of another link 236 or 237b (not shown) can be positioned in the slots 323-1, 323-2, such that the other link (not shown) must be rotated 90 degrees in order to mate with the first link 236, and will rotate about the second axis B perpendicular to the first axis A. Multiple links connected in this fashion allow the articulation region 235 to have 2 degrees of freedom.

FIG. 7A-7E are views of an articulating surgical instrument 200 in various positions, in accordance with an embodiment. Tension or slack provided to one or more steering cables 410a-d (generally, 410) can permit an operator to change the articulation state of the surgical instrument 200.

Figure 7A:
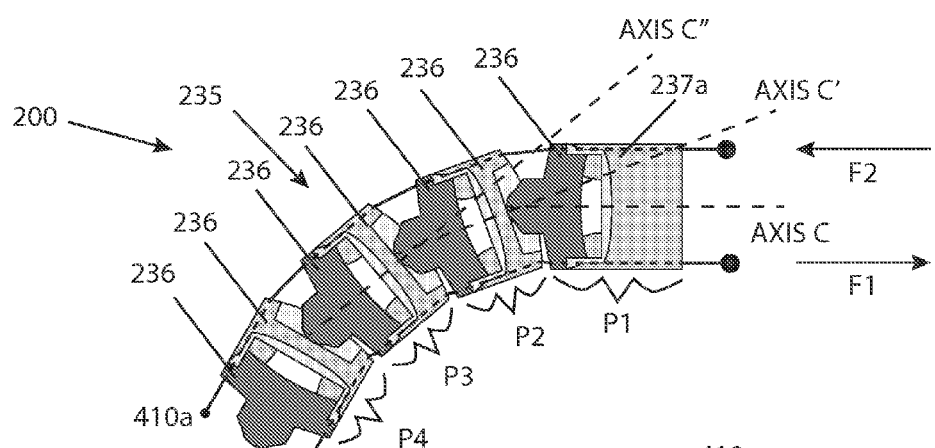
FIG. 7A-7E are views of an articulating surgical instrument in various positions, in accordance with an embodiment.

As shown in FIG. 7A, tension can be applied to a first steering cable 410a, for example, a horizontal steering cable or a vertical steering cable described herein. Here, an operator can apply a force F1, i.e., tension, to a second steering cable 410b to bend the articulation region 235 to a desired angle of articulation. A force F2, for example, slack, can be applied to a first steering cable 410a. The operator can maintain the angle of articulation until a different force is applied to the articulation cables 410. Continuing with this example, the operator can independently apply tension or slack to an actuation cable described herein (not shown), for example, to open and close a grasper at a functional element (not shown) at a distal end of the articulation region 235, while the tool shaft is maintained at the angle of articulation. The operator can alternatively open and close the grasper while also bending the surgical instrument 200.

Figure 7B:
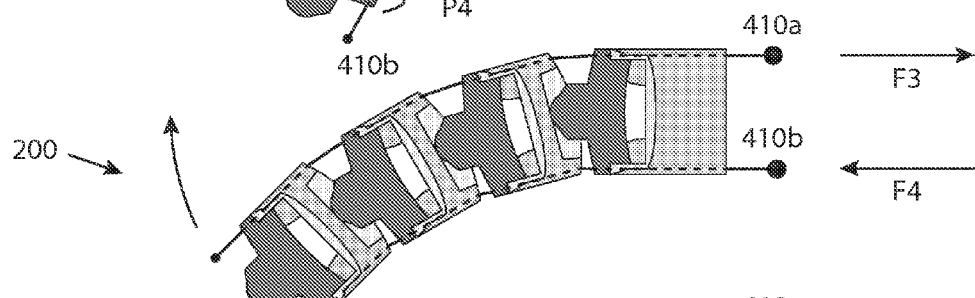
Figure 7C:
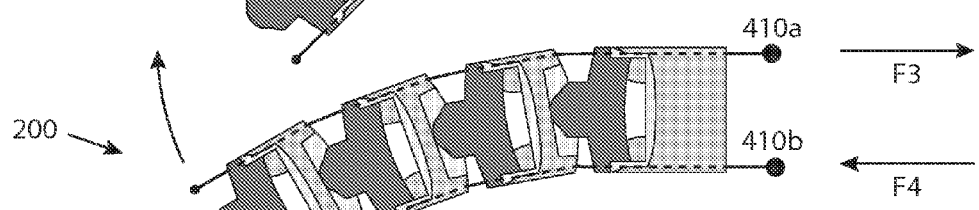
Figure 7D:
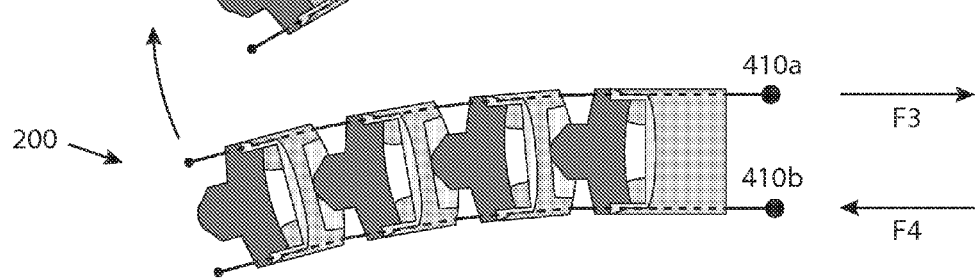
Figure 7E:
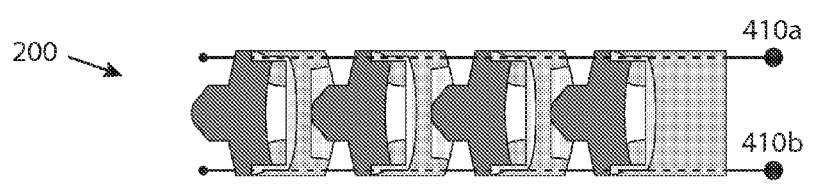

As shown in FIGS. 7B-7D, the articulation region 235 can be moved in an upward direction by applying tension F3 to the first steering cable 410a, and providing slack F4 to the second steering cable 410b. In doing so, one or more pairs P1-P4 of adjacent links can move according to a single degree of freedom due to the relationship between protrusions 322 and slots 323 of the paired links 236, resulting in the articulation region 235 to move in a single plane of motion, for example, in an up direction.

FIG. 8 is a cutaway side view of a distal end of a surgical instrument 200, in accordance with an embodiment, which can include an end effector 250, such as a grasper, and a portion of the articulation region 235. The end effector 250 is constructed and arranged to rotate with respect to a distal segment 604 of the articulating region 235, for example as has been described herein.

A slide 801 can be positioned between the end effector 250 and the distal segment 604. An end effector housing 251 can be positioned about some or all of the slides 801.

Distal ends of the steering cables 410 can be secured with an outer sleeve 804 positioned over a portion of the distal segment 604. More specifically, the distal ends of the steering cables 410 are positioned in a cable notch 812 at the distal segment 604, secured within the outer sleeve 804.

The end effector 250 is fixedly attached to the support element 231, which runs the length of the instrument 200 from a rotation knob in the handle (not shown) of the instrument 200. An activation element 420 extends through the support element 231 runs a length of the instrument 200 from a translating assembly (not shown) in the handle. A translation of the activation element 420 controls the movement of the end effector 250, for example, permitting a tool such as a grasper of the end effector 250 to open and close.

A tension applied to the activation element 420 retracts the slide 801 into a recess 805 at the functional element housing 251. This slide 801 operates a mechanism which closes the end effector 250 about a hinge point 807. A pushing force on the activation element 420 moves the slide 801 distally, thereby opening the end effector 250. The housing 251 is slidingly received by a recess 809 in the distal segment 604. The housing 251 can be coupled to the distal end of the support element 231, for example, using an adhesive, or by welding, swaging, threading, pinning, snap-fitting, press-fitting, or coupling together in a well-known manner to those of ordinary skill in the art. The housing 251 is configured to freely rotate within this recess 809, such that rotation of the support element 231 in turn rotates the effector housing 251. A longitudinal clearance 839 is dimensioned in an axial direction of the surgical instrument, and can provide for play, or "wiggle room" between the housing 251 and the distal segment 604 to prevent contact between the housing 251 and a distal end of the articulation region 235, for example, the distal segment 604, when a force is imparted by the movement of the activation element 420.

While the present inventive concepts have been particularly shown and described above with reference to exemplary embodiments thereof, it will be understood by those of ordinary skill in the art, that various changes in form and detail can be made without departing from the spirit and scope of the present inventive concepts described and defined by the following at least one of the preceding claims.

What is claimed is:

1. A surgical instrument comprising:
  a steering mechanism, comprising:
    a handle at a proximal end of the surgical instrument, the handle including a plurality of controls for controlling a movement of the surgical instrument; and
    a hub that rotatably mates with the handle; and
  a housing positioned about the hub, wherein the handle, the housing, and the hub communicate with each other to provide at least a first degree of freedom and a second degree of freedom, the surgical instrument further comprising an articulation region at a distal end of the surgical instrument, wherein a movement of the steering mechanism handle in one and only one of the first or second degrees of freedom relative to at least one of the housing or the hub translates to a movement of the articulation region in a single plane of motion,
  wherein the steering mechanism further comprises a locking mechanism controlled by at least one locking control of the plurality of controls of the handle, the locking mechanism constructed and arranged to disable one of the first and second degrees of freedom to limit a movement of the articulation region in the single plane of motion, and
  wherein the locking mechanism includes a first lock that prevents the steering mechanism from articulating with the first degree of freedom and a second lock that prevents the steering mechanism from articulating with the second degree of freedom
  wherein the hub includes a first post and a second post along a first articulating axis, and wherein the first lock includes a first locking ring and a first cam clamp that applies a force to the first locking ring, which prevents the housing from rotating about the first articulating axis
  wherein the hub includes a third post and a fourth post along a second articulating axis orthogonal to the first articulating axis, and wherein the second lock includes a second locking ring and a second cam clamp that applies a force to the second locking ring, which prevents the housing from rotating about the second articulating axis.

2. The surgical instrument of claim 1, wherein the locking mechanism comprises two locking mechanisms controlled by the at least one locking control, and wherein the two locking mechanisms, when activated, are constructed and arranged to disable one or both of the first and second degrees of freedom to prevent steering of the articulation region.

3. The surgical instrument of claim 1, further comprising a set of first interdigitating teeth between the first locking ring and the housing, wherein the first locking ring applies a force at the first interdigitating teeth to prevent a rotation of the housing about the first articulating axis.

4. The surgical instrument of claim 3, further comprising a set of second interdigitating teeth between the second locking ring and the housing, wherein the second locking ring applies a force at the second interdigitating teeth to prevent a rotation of the handle about the second articulating axis.

5. The surgical instrument of claim 1, wherein the first articulating axis is a vertical axis, and wherein a rotation of the hub about the vertical axis provides a horizontal control of the steerable portion.

6. The surgical instrument of claim 1, wherein the second articulating axis is a horizontal axis, and wherein a rotation of the handle about the horizontal axis of the hub provides a vertical control of the articulation region.

7. The surgical instrument of claim 1, wherein an activation of either the first lock or the second lock limits movement of the articulation region to the single plane of motion.

8. The surgical instrument of claim 1, wherein an activation of both the first lock and the second lock prevents steering of the instrument, and maintains a tool at a distal end of the instrument tool in a current position.

9. The surgical instrument of claim 1, wherein the first lock and the second lock are disengaged, and the articulation region articulates in multiple planes of motion.

10. The surgical instrument of claim 1, wherein the instrument comprises an end effector coupled to the articulation region, and wherein an articulation of the handle in accordance with two degrees of freedom permits the articulation region to be manipulated to reach anywhere on a surface of at least a partial sphere.

11. The surgical instrument of claim 10, wherein the plurality of controls at the handle includes a ratcheting trigger for incrementally ratcheting the end effector at the distal end of the instrument.

12. The surgical instrument of claim 1, further comprising a plurality of steering cables coupled between the housing and the articulation region, wherein articulation of the handle relative to the housing advances and retracts the plurality of steering cables, which move the articulation region in the single plane of motion or in multiple planes of motion.

13. The surgical instrument of claim 12, wherein the plurality of steering cables comprise first and second steering cables that extend from the handle to the articulation region, the first and second steering cables constructed and arranged to move the articulation region relative to a first axis about the single plane of motion when the handle articulates at the first degree of freedom relative to the housing.

14. The surgical instrument of claim 13, wherein the articulation region moves in the single plane of motion in response to a movement of at least one of the first or second steering cables in an axial direction between the handle and the articulation region.

15. The surgical instrument of claim 14, wherein the movement of the at least one of the first or second steering cables in the axial direction is in response to a movement by the handle relative to the housing at the first degree of freedom.

16. The surgical instrument of claim 13, wherein the hub includes first and second cable fastening locations that couple proximal ends of the first and second steering cables to the hub.

17. The surgical instrument of claim 13, further comprising third and fourth steering cables that extend from the handle to the articulation region, the third and fourth steering cables constructed and arranged to move the articulation region about a second axis orthogonal to the first axis.

18. The surgical instrument of claim 17, wherein the articulation region moves in the single plane of motion in response to a movement of at least one of the third or fourth steering cables in an axial direction between the handle and the articulation region.

19. The surgical instrument of claim 18, wherein the movement of the at least one of the third or fourth steering cables in the axial direction is in response to a movement by the handle relative to the hub in the second degree of freedom orthogonal to the first degree of freedom.

20. The surgical instrument of claim 17, wherein the hub includes first and second cable pass-through holes and the handle includes first and second fastening locations, wherein the third and fourth steering cables extend through the first and second pass-through holes, respectively, and wherein proximal ends of the third and fourth steering cables are coupled to the handle.

21. The surgical instrument of claim 17, wherein the handle includes a cable tensioning mechanism that adjusts a tension of the third and fourth steering cables at the proximal ends.

22. The surgical instrument of claim 21, wherein the cable tensioning mechanism comprises a set screw movably positioned in a threaded socket in the housing, the set screw including an opening for receiving an end of at least one of the third or fourth steering cables, which is secured to the set screw.

23. The surgical instrument of claim 22, wherein the cable tensioning mechanism further comprising a tightening tool that adjusts the position of the set screw relative to the socket to achieve a desired tension of the at least one of the third or fourth steering cables.

24. The surgical instrument of claim 1, further comprising a support element having a proximal end coupled to the handle, a portion of the support element extending through the articulation region, the support element constructed and arranged to rotate independently of the movement of the articulation region in the single plane of motion.

25. The surgical instrument of claim 24, wherein the support element is constructed and arranged as a coil.

26. The surgical instrument of claim 24, wherein the support element is constructed and arranged as a hollow tube.

27. The surgical instrument of claim 24, further comprising a clevis between an end effector coupled to the articulation region and a distal end of the support element.

28. The surgical instrument of claim 1, wherein the steering mechanism further comprises a ratchet mechanism, a gearing mechanism, a trigger assembly, and a translating assembly, wherein the ratchet mechanism is configured to maintain the translating assembly in a series of linear positions.

29. The surgical instrument of claim 1, further comprising an end effector coupled to the articulation region at the distal end of the surgical instrument.

30. The surgical instrument of claim 29, wherein the end effector includes a housing and at least one tool.

31. The surgical instrument of claim 30, wherein the at least one tool comprises at least one of: a grasper; a scissor; a cutter; a claw; or a knife.

32. The surgical instrument of claim 30, wherein the at least one tool comprises at least one of: an ablator, a drug delivery apparatus, a radiation source, an EKG electrode, a pressure sensor, a blood sensor, a camera, a magnet, a heating element, an energy delivery element, and a cryogenic element.

33. The surgical instrument of claim 30, further comprising a support element that extends along at least a portion of the instrument, through a central working channel of the articulation region, and terminates at the end effector housing.

* * * * *